(12) United States Patent
Leadley et al.

(10) Patent No.: US 11,241,043 B2
(45) Date of Patent: Feb. 8, 2022

(54) VAPOR PROVISION APPARATUS

(71) Applicant: NICOVENTURES HOLDINGS LIMITED, London (GB)

(72) Inventors: David Leadley, London (GB); Jeremy Wright, London (GB)

(73) Assignee: Nicoventures Trading Limited, London (GB)

( * ) Notice: Subject to any disclaimer, the term of this patent is extended or adjusted under 35 U.S.C. 154(b) by 195 days.

(21) Appl. No.: 16/087,019

(22) PCT Filed: Mar. 21, 2017

(86) PCT No.: PCT/GB2017/050783
§ 371 (c)(1),
(2) Date: Sep. 20, 2018

(87) PCT Pub. No.: WO2017/163046
PCT Pub. Date: Sep. 28, 2017

(65) Prior Publication Data
US 2019/0083720 A1    Mar. 21, 2019

(30) Foreign Application Priority Data

Mar. 24, 2016    (GB) ..................... 1605105

(51) Int. Cl.
*A24F 40/48*    (2020.01)
*A24F 40/485*    (2020.01)
(Continued)

(52) U.S. Cl.
CPC ......... *A24F 40/485* (2020.01); *A61M 11/042* (2014.02); *A61M 15/06* (2013.01);
(Continued)

(58) Field of Classification Search
CPC ........................... A24F 47/008; A24F 40/485
See application file for complete search history.

(56) References Cited

U.S. PATENT DOCUMENTS 3,614,956 A    10/1971  Thornton et al.
3,888,253 A    6/1975   Watt et al.
(Continued)

FOREIGN PATENT DOCUMENTS

AT          508244 A4    12/2010
AU       2017236411 B2     6/2019
(Continued)

OTHER PUBLICATIONS

Decision dated Mar. 14, 2017 for Ukrainian Application No. S201601341, 7 pages.
(Continued)

*Primary Examiner* — James Harvey
(74) *Attorney, Agent, or Firm* — Patterson Thuente Pedersen, P.A.

(57) ABSTRACT

A vapor provision apparatus including a vapor generation chamber containing a vaporizer for generating vapor from a vapor precursor material; and an air channel wall defining an air channel between the vapor generation chamber and a vapor outlet at a mouthpiece end of the vapor provision apparatus through which a user can inhale vapor during use; wherein an inner surface of the air channel wall is provided with at least one protrusion extending into the air channel to modify (redirect) a flow of air in the air channel during use. For example, the at least one protrusion may be arranged to define one or more portions of a helical wall extending into the air channel so as to impart a degree of rotation about an axis of extent of the air channel to air flowing in the air channel during use.

18 Claims, 11 Drawing Sheets

(51) Int. Cl.
*A61M 15/06* (2006.01)
*A61M 11/04* (2006.01)
A24F 40/10 (2020.01)
A24F 40/20 (2020.01)

(52) U.S. Cl.
CPC ............... *A24F 40/10* (2020.01); *A24F 40/20* (2020.01); *A61M 2206/14* (2013.01)

(56) References Cited

U.S. PATENT DOCUMENTS

| | | |
|---|---|---|
| 4,022,221 A | 5/1977 | Berger |
| D250,485 S | 12/1978 | Cuthbertson |
| 4,517,996 A | 5/1985 | Vester |
| 4,602,647 A | 7/1986 | Wiethaup et al. |
| 4,655,229 A | 4/1987 | Sensabaugh, Jr. et al. |
| 4,945,929 A | 8/1990 | Egilmex |
| D367,526 S | 2/1996 | Bignon |
| 5,564,442 A | 10/1996 | MacDonald et al. |
| D430,358 S | 8/2000 | Papiernik |
| 6,182,655 B1 | 2/2001 | Keller et al. |
| D447,276 S | 8/2001 | Gustafson |
| 6,418,926 B1 | 7/2002 | Chawla |
| 6,446,880 B1 | 9/2002 | Schram et al. |
| D466,644 S | 12/2002 | Cohen Harel |
| D469,962 S | 2/2003 | Campbell et al. |
| D503,996 S | 4/2005 | Mabbutt |
| D504,947 S | 5/2005 | McAuley et al. |
| D505,514 S | 5/2005 | Liu |
| D514,222 S | 1/2006 | Anderson et al. |
| D518,171 S | 3/2006 | Anderson et al. |
| D560,793 S | 1/2008 | Pearl et al. |
| D569,967 S | 5/2008 | Pearl et al. |
| D572,406 S | 7/2008 | Masoud |
| D577,815 S | 9/2008 | Gokhale et al. |
| D579,544 S | 10/2008 | Birath et al. |
| D579,545 S | 10/2008 | Birath et al. |
| D579,546 S | 10/2008 | Birath et al. |
| D579,547 S | 10/2008 | Birath et al. |
| D579,548 S | 10/2008 | Birath et al. |
| D579,549 S | 10/2008 | Birath et al. |
| D579,550 S | 10/2008 | Birath et al. |
| D581,520 S | 11/2008 | Williams et al. |
| D583,463 S | 12/2008 | Wood et al. |
| D590,495 S | 4/2009 | Lulla et al. |
| D590,938 S | 4/2009 | Lulla et al. |
| D591,856 S | 5/2009 | Lulla et al. |
| D613,848 S | 4/2010 | Harvey et al. |
| D614,285 S | 4/2010 | Birath et al. |
| D629,886 S | 12/2010 | Adamo et al. |
| D637,280 S | 5/2011 | Harvey et al. |
| D637,281 S | 5/2011 | Harvey et al. |
| D637,282 S | 5/2011 | Harvey et al. |
| D639,414 S | 6/2011 | Berndt |
| D641,076 S | 7/2011 | Grunstad et al. |
| D646,780 S | 10/2011 | Lulla et al. |
| D659,236 S | 5/2012 | Bobjer et al. |
| D670,374 S | 11/2012 | Bobjer et al. |
| D671,207 S | 11/2012 | Bobjer et al. |
| D684,254 S | 6/2013 | Zuyderhoudt |
| D684,684 S | 6/2013 | Grunstad et al. |
| D692,997 S | 11/2013 | Lovell et al. |
| D693,963 S | 11/2013 | Akopyan |
| 8,602,210 B2 | 12/2013 | Milner et al. |
| D700,227 S | 2/2014 | Kile |
| D700,738 S | 3/2014 | Rennick et al. |
| D710,002 S | 7/2014 | Valentine et al. |
| D711,528 S | 8/2014 | Grunstad et al. |
| D717,425 S | 11/2014 | Von Schuckmann |
| D726,364 S | 4/2015 | Weigensberg |
| D726,955 S | 4/2015 | Martin |
| D737,419 S | 8/2015 | Emarlou |
| D737,426 S | 8/2015 | Nakamura |
| 9,155,336 B2 | 10/2015 | Liu |
| D745,139 S | 12/2015 | Chen et al. |
| D745,660 S | 12/2015 | Gruntad et al. |
| D761,488 S | 7/2016 | Alarcon et al. |
| D769,438 S | 10/2016 | Crosby et al. |
| D770,088 S | 10/2016 | Abadi et al. |
| D782,109 S | 3/2017 | King |
| D790,123 S | 6/2017 | Beer et al. |
| D790,125 S | 6/2017 | Beer et al. |
| D790,767 S | 6/2017 | Rush et al. |
| D799,750 S | 10/2017 | Parcevaux |
| 9,956,357 B2 | 5/2018 | Chen |
| 9,964,300 B2 | 5/2018 | Liu |
| D820,514 S | 6/2018 | Durand |
| D820,515 S | 6/2018 | Nettenstrom et al. |
| D822,193 S | 7/2018 | Nitta |
| 10,010,109 B2 | 7/2018 | Janardhan et al. |
| 10,058,122 B2 | 8/2018 | Steingraber et al. |
| D852,408 S | 6/2019 | Nettenstrom et al. |
| 10,653,186 B2 | 5/2020 | Verleur et al. |
| 2002/0040713 A1 | 4/2002 | Eisele et al. |
| 2003/0178024 A1 | 9/2003 | Allan et al. |
| 2003/0235538 A1 | 12/2003 | Zierenberg |
| 2004/0003820 A1 | 1/2004 | Iannuzzi |
| 2004/0025865 A1 | 2/2004 | Nichols et al. |
| 2004/0025877 A1 | 2/2004 | Crowder |
| 2004/0118936 A1 | 6/2004 | Schram et al. |
| 2004/0149283 A1 | 8/2004 | Hochrainer |
| 2004/0244810 A1 | 12/2004 | Henninger et al. |
| 2005/0005934 A1 | 1/2005 | Harvey |
| 2005/0006273 A1 | 1/2005 | Chawla |
| 2005/0017017 A1 | 1/2005 | Crosby et al. |
| 2005/0022812 A1 | 2/2005 | Hrkach |
| 2005/0103336 A1 | 5/2005 | Nishibayashi et al. |
| 2005/0103337 A1 | 5/2005 | Hickey et al. |
| 2005/0115562 A1 | 6/2005 | Chawla |
| 2005/0205685 A1 | 9/2005 | Jones |
| 2005/0252511 A1 | 11/2005 | Pentafragas |
| 2005/0279357 A1 | 12/2005 | Wachtel |
| 2006/0102175 A1 | 5/2006 | Nelson |
| 2006/0157053 A1 | 7/2006 | Barney et al. |
| 2006/0157054 A1 | 7/2006 | Kuehn et al. |
| 2006/0163269 A1 | 7/2006 | Anderson et al. |
| 2006/0237010 A1 | 10/2006 | De Boer et al. |
| 2006/0237016 A1 | 10/2006 | Wachtel |
| 2007/0045288 A1 | 3/2007 | Nelson |
| 2007/0052544 A1 | 3/2007 | Lintell |
| 2007/0102016 A1 | 5/2007 | Xiahou |
| 2007/0114305 A1 | 5/2007 | Yamaguchi et al. |
| 2007/0125765 A1 | 6/2007 | Nelson |
| 2007/0131805 A1 | 6/2007 | Yamaguchi et al. |
| 2007/0137645 A1 | 6/2007 | Eason et al. |
| 2007/0152086 A1 | 7/2007 | Yamaguchi et al. |
| 2007/0181123 A1 | 8/2007 | Houzego |
| 2007/0215149 A1 | 9/2007 | King et al. |
| 2007/0267032 A1 | 11/2007 | Shan |
| 2007/0295332 A1 | 12/2007 | Ziegler et al. |
| 2008/0099015 A1 | 5/2008 | Pocock et al. |
| 2008/0116220 A1 | 5/2008 | Pocock et al. |
| 2008/0196718 A1 | 8/2008 | Connell et al. |
| 2008/0295832 A1 | 12/2008 | Geser et al. |
| 2008/0295834 A1 | 12/2008 | Thoemmes et al. |
| 2008/0314384 A1 | 12/2008 | Harris et al. |
| 2009/0084379 A1 | 4/2009 | Goeckner et al. |
| 2009/0165791 A1 | 7/2009 | Wendland |
| 2009/0194105 A1 | 8/2009 | Besseler et al. |
| 2009/0205656 A1 | 8/2009 | Nishibayashi et al. |
| 2009/0250056 A1 | 10/2009 | Pentafragas |
| 2009/0277446 A1 | 11/2009 | Walz |
| 2009/0283095 A1 | 11/2009 | Pocock et al. |
| 2009/0293888 A1 | 12/2009 | Williams et al. |
| 2009/0293892 A1 | 12/2009 | Williams et al. |
| 2009/0314291 A1 | 12/2009 | Anderson et al. |
| 2010/0024812 A1 | 2/2010 | Sugita et al. |
| 2010/0024814 A1 | 2/2010 | Sugita et al. |
| 2010/0059050 A1 | 3/2010 | Wachtel |
| 2010/0059052 A1 | 3/2010 | Davies et al. |
| 2010/0078022 A1 | 4/2010 | Striebig et al. |
| 2010/0083962 A1 | 4/2010 | Von Schuckmann |
| 2010/0154795 A1 | 6/2010 | Pentafragas |
| 2010/0163042 A1 | 7/2010 | Bhowmick et al. |

(56) References Cited

U.S. PATENT DOCUMENTS

| | | |
|---|---|---|
| 2010/0189780 A1 | 7/2010 | Walz et al. |
| 2010/0192949 A1 | 8/2010 | Wright et al. |
| 2010/0242960 A1 | 9/2010 | Zangerle |
| 2010/0258120 A1 | 10/2010 | Colomb |
| 2010/0294278 A1 | 11/2010 | Mosier et al. |
| 2010/0313886 A1 | 12/2010 | Wachtel et al. |
| 2011/0036346 A1 | 2/2011 | Cohen et al. |
| 2011/0041841 A1 | 2/2011 | Wachtel et al. |
| 2011/0067696 A1 | 3/2011 | Sato et al. |
| 2011/0094523 A1 | 4/2011 | Thorens et al. |
| 2011/0120463 A1 | 5/2011 | Esteve et al. |
| 2011/0120465 A1 | 5/2011 | Haerder et al. |
| 2011/0162642 A1 | 7/2011 | Akouka et al. |
| 2011/0174305 A1 | 7/2011 | Bunch et al. |
| 2011/0203586 A1 | 8/2011 | Egen et al. |
| 2011/0226236 A1 | 9/2011 | Buchberger |
| 2011/0232637 A1 | 9/2011 | Kaemper et al. |
| 2011/0271958 A1 | 11/2011 | Sawant |
| 2011/0277757 A1 | 11/2011 | Terry et al. |
| 2011/0277760 A1 | 11/2011 | Terry et al. |
| 2012/0037157 A1 | 2/2012 | Rohrschneider et al. |
| 2012/0037158 A1 | 2/2012 | Wachtel et al. |
| 2012/0132205 A1 | 5/2012 | Meliniotis et al. |
| 2012/0247463 A1 | 10/2012 | Zoltan |
| 2012/0260917 A1 | 10/2012 | Bilgic |
| 2013/0047985 A1 | 2/2013 | Harris et al. |
| 2013/0074857 A1 | 3/2013 | Buchberger |
| 2013/0139815 A1 | 6/2013 | Colomb et al. |
| 2013/0152927 A1 | 6/2013 | Baillet et al. |
| 2013/0152928 A1 | 6/2013 | Kirniak |
| 2013/0174842 A1 | 7/2013 | Young et al. |
| 2013/0186398 A1 | 7/2013 | Baillet et al. |
| 2013/0192615 A1 | 8/2013 | Tucker et al. |
| 2013/0228191 A1 | 9/2013 | Newton |
| 2013/0233313 A1 | 9/2013 | Young et al. |
| 2013/0255679 A1 | 10/2013 | Andrade et al. |
| 2013/0269695 A1 | 10/2013 | Brouet et al. |
| 2013/0306065 A1 | 11/2013 | Thorens et al. |
| 2014/0000601 A1 | 1/2014 | Arvidsson et al. |
| 2014/0007875 A1 | 1/2014 | Berg et al. |
| 2014/0076315 A1 | 3/2014 | Von Schuckmann |
| 2014/0083422 A1 | 3/2014 | Arvidsson et al. |
| 2014/0109921 A1 | 4/2014 | Chen |
| 2014/0123989 A1 | 5/2014 | LaMothe |
| 2014/0196717 A1 | 7/2014 | Liu |
| 2014/0238422 A1 | 8/2014 | Plunkett et al. |
| 2014/0238424 A1 | 8/2014 | Macko et al. |
| 2014/0290653 A1 | 10/2014 | Colomb |
| 2014/0299125 A1 | 10/2014 | Buchberger |
| 2014/0318538 A1 | 10/2014 | Bilgic |
| 2014/0360514 A1 | 12/2014 | Zhu |
| 2014/0376895 A1 | 12/2014 | Han |
| 2015/0027454 A1* | 1/2015 | Li ............... A61M 11/044 131/328 |
| 2015/0027456 A1* | 1/2015 | Janardhan ......... A24F 47/008 131/328 |
| 2015/0027457 A1 | 1/2015 | Janardhan et al. |
| 2015/0034104 A1 | 2/2015 | Zhou |
| 2015/0059747 A1 | 3/2015 | Von Schuckmann |
| 2015/0068541 A1 | 3/2015 | Sears et al. |
| 2015/0080808 A1 | 3/2015 | Esteve et al. |
| 2015/0083129 A1 | 3/2015 | Colomb et al. |
| 2015/0086804 A1 | 3/2015 | Schorn et al. |
| 2015/0096563 A1 | 4/2015 | Toksoz et al. |
| 2015/0107590 A1 | 4/2015 | Colomb |
| 2015/0114391 A1 | 4/2015 | Colomb et al. |
| 2015/0114393 A1 | 4/2015 | Von Schuckmann |
| 2015/0122276 A1 | 5/2015 | Johnson et al. |
| 2015/0122277 A1 | 5/2015 | Frobisher et al. |
| 2015/0128938 A1 | 5/2015 | Colomb et al. |
| 2015/0128977 A1 | 5/2015 | Li et al. |
| 2015/0144145 A1 | 5/2015 | Chang et al. |
| 2015/0144147 A1 | 5/2015 | Li et al. |
| 2015/0164142 A1 | 6/2015 | Li et al. |
| 2015/0174346 A1 | 6/2015 | Dhuppad et al. |
| 2015/0208730 A1 | 7/2015 | Li et al. |
| 2015/0216237 A1 | 8/2015 | Wensley et al. |
| 2015/0257446 A1 | 9/2015 | Chung |
| 2015/0297841 A1 | 10/2015 | Ono |
| 2015/0298893 A1 | 10/2015 | Welp |
| 2015/0314085 A1 | 11/2015 | Banoun |
| 2015/0320116 A1 | 11/2015 | Bleloch et al. |
| 2015/0335075 A1 | 11/2015 | Minskoff et al. |
| 2015/0342256 A1 | 12/2015 | Chen |
| 2015/0343159 A1 | 12/2015 | Farr et al. |
| 2016/0001018 A1 | 1/2016 | Fink et al. |
| 2016/0001019 A1 | 1/2016 | Fink et al. |
| 2016/0007654 A1 | 1/2016 | Zhu |
| 2016/0015082 A1 | 1/2016 | Liu |
| 2016/0015912 A1 | 1/2016 | De Kruijf et al. |
| 2016/0021934 A1 | 1/2016 | Cadieux et al. |
| 2016/0022931 A1 | 1/2016 | Althorpe et al. |
| 2016/0045684 A1 | 2/2016 | Ono |
| 2016/0050975 A1 | 2/2016 | Worm et al. |
| 2016/0109115 A1 | 4/2016 | Lipowicz |
| 2016/0128386 A1 | 5/2016 | Chen |
| 2016/0143365 A1 | 5/2016 | Liu |
| 2016/0151589 A1 | 6/2016 | Ohrt et al. |
| 2016/0158470 A1 | 6/2016 | Esteve et al. |
| 2016/0175547 A1 | 6/2016 | Nakamura |
| 2016/0219936 A1 | 8/2016 | Alarcon |
| 2016/0264290 A1 | 9/2016 | Hafer et al. |
| 2016/0279354 A1 | 9/2016 | De Kruijf et al. |
| 2016/0287818 A1 | 10/2016 | Colomb et al. |
| 2016/0338411 A1 | 11/2016 | Liu |
| 2016/0346488 A1 | 12/2016 | Beller |
| 2016/0367767 A1 | 12/2016 | Cashman et al. |
| 2016/0375207 A1 | 12/2016 | Bhide et al. |
| 2017/0035117 A1 | 2/2017 | Lin |
| 2017/0056608 A1 | 3/2017 | McDerment et al. |
| 2017/0064999 A1 | 3/2017 | Perez et al. |
| 2017/0119057 A1 | 5/2017 | Liu |
| 2017/0127728 A1 | 5/2017 | Li et al. |
| 2017/0208866 A1 | 7/2017 | Liu |
| 2017/0231281 A1 | 8/2017 | Hatton et al. |
| 2017/0231282 A1 | 8/2017 | Bowen et al. |
| 2017/0280773 A1 | 10/2017 | Force |
| 2017/0280778 A1 | 10/2017 | Force |
| 2017/0325504 A1 | 11/2017 | Liu |
| 2017/0360092 A1 | 12/2017 | Althorpe et al. |
| 2018/0007960 A1 | 1/2018 | Suzuki et al. |
| 2018/0035718 A1 | 2/2018 | Liu |
| 2018/0213845 A1* | 8/2018 | Qiu ................. H05B 3/03 |
| 2018/0220708 A1* | 8/2018 | Scott .............. A24F 47/004 |
| 2018/0228216 A1 | 8/2018 | Saygili |
| 2018/0352867 A1* | 12/2018 | Kane ............... A24F 47/008 |
| 2019/0022345 A1* | 1/2019 | Kotch ............. A61M 16/145 |
| 2019/0046745 A1* | 2/2019 | Nettenstrom ...... A61M 11/042 |
| 2019/0053542 A1* | 2/2019 | Chen .............. A61M 11/042 |
| 2019/0083720 A1* | 3/2019 | Leadley ........... A61M 15/06 |
| 2019/0098931 A1* | 4/2019 | Leadley ........... A61M 15/06 |
| 2019/0230991 A1* | 8/2019 | Liu ................. A24F 47/00 |
| 2020/0138117 A1 | 5/2020 | Rosser et al. |
| 2020/0146360 A1 | 5/2020 | Rosser |
| 2020/0154770 A1 | 5/2020 | Hepworth et al. |
| 2020/0281270 A1 | 9/2020 | Potter et al. |
| 2020/0367557 A1* | 11/2020 | Lin ................. A24F 40/42 |
| 2020/0375263 A1* | 12/2020 | Chen ............... H05B 1/0297 |

FOREIGN PATENT DOCUMENTS

| | | |
|---|---|---|
| AU | 2017236564 B2 | 11/2019 |
| CA | 2505366 A1 | 10/2006 |
| CL | 2018002640 A1 | 12/2018 |
| CL | 2018002657 A1 | 12/2018 |
| CL | 2018002658 A1 | 12/2018 |
| CN | 2698098 Y | 5/2005 |
| CN | 2827020 Y | 10/2006 |
| CN | 1906096 A | 1/2007 |
| CN | 300865525 | 9/2007 |
| CN | 300840847 | 10/2008 |
| CN | 300867097 | 12/2008 |
| CN | 101400397 A | 4/2009 |
| CN | 101468218 A | 7/2009 |

(56) References Cited

FOREIGN PATENT DOCUMENTS

| | | |
|---|---|---|
| CN | 101574552 A | 11/2009 |
| CN | 301347038 S | 12/2009 |
| CN | 301433957 S | 6/2010 |
| CN | 201791251 U | 4/2011 |
| CN | 202085710 U | 12/2011 |
| CN | 302012774 S | 3/2012 |
| CN | 102655773 A | 9/2012 |
| CN | 302216014 S | 12/2012 |
| CN | 103118726 A | 5/2013 |
| CN | 103237570 A | 8/2013 |
| CN | 302926278 S | 1/2014 |
| CN | 203492795 U | 3/2014 |
| CN | 203523806 U | 4/2014 |
| CN | 203872998 U | 10/2014 |
| CN | 104254258 A | 12/2014 |
| CN | 204015104 U | 12/2014 |
| CN | 104544567 A | 4/2015 |
| CN | 104544570 A | 4/2015 |
| CN | 303162040 S | 4/2015 |
| CN | 303192526 S | 4/2015 |
| CN | 104605482 A | 5/2015 |
| CN | 204317491 U | 5/2015 |
| CN | 303227659 S | 5/2015 |
| CN | 303417607 | 5/2015 |
| CN | 104720114 A | 6/2015 |
| CN | 303234670 S | 6/2015 |
| CN | 303250845 S | 6/2015 |
| CN | 303442703 S | 6/2015 |
| CN | 303535276 S | 6/2015 |
| CN | 104770882 A | 7/2015 |
| CN | 204426686 U | 7/2015 |
| CN | 204444245 U | 7/2015 |
| CN | 303273075 S | 7/2015 |
| CN | 303279026 S | 7/2015 |
| CN | 303300421 S | 7/2015 |
| CN | 303300422 S | 7/2015 |
| CN | 104824846 A | 8/2015 |
| CN | 204519363 U | 8/2015 |
| CN | 303322969 S | 8/2015 |
| CN | 303322971 S | 8/2015 |
| CN | 303322985 S | 8/2015 |
| CN | 303341926 S | 8/2015 |
| CN | 303350911 S | 8/2015 |
| CN | 104921308 A | 9/2015 |
| CN | 204617062 U | 9/2015 |
| CN | 303361183 S | 9/2015 |
| CN | 303380240 S | 9/2015 |
| CN | 303380242 S | 9/2015 |
| CN | 303380243 S | 9/2015 |
| CN | 303380252 S | 9/2015 |
| CN | 303417611 S | 10/2015 |
| CN | 105011380 A | 11/2015 |
| CN | 303470028 S | 11/2015 |
| CN | 105455197 A | 4/2016 |
| CN | 105455197 B | 1/2019 |
| DE | 95102980001 | 9/1996 |
| DE | 96072850001 | 4/1997 |
| DE | 96072850002 | 4/1997 |
| DE | 499019970001 | 7/1999 |
| DE | 499019970002 | 7/1999 |
| DE | 400039090001 | 8/2000 |
| DE | 401071010001 | 2/2002 |
| DE | 402003030001 | 8/2002 |
| DE | 402093100001 | 3/2003 |
| DE | 402093100002 | 3/2003 |
| DE | 402093100003 | 3/2003 |
| DE | 402093100004 | 3/2003 |
| DE | 402093100005 | 3/2003 |
| DE | 403019480001 | 7/2003 |
| DE | 202013010929 U1 | 12/2013 |
| DE | 96072850003 | 3/2016 |
| EA | 019736 B1 | 5/2014 |
| EM | 0001050440001 | 6/2003 |
| EM | 0001050440002 | 6/2003 |
| EM | 0005457690001 | 6/2006 |
| EM | 0007369620001 | 6/2007 |
| EM | 0007369620002 | 6/2007 |
| EM | 0007369620003 | 6/2007 |
| EM | 0007369620004 | 6/2007 |
| EM | 0007369620005 | 6/2007 |
| EM | 0007369620006 | 6/2007 |
| EM | 0007369620007 | 6/2007 |
| EM | 0007369620008 | 6/2007 |
| EM | 0008611410001 | 1/2008 |
| EM | 0015105870001 | 5/2009 |
| EM | 0015105870002 | 5/2009 |
| EM | 0013233070007 | 4/2012 |
| EM | 0013233070008 | 4/2012 |
| EM | 0013233070009 | 4/2012 |
| EM | 0013233070010 | 4/2012 |
| EM | 0013233070011 | 4/2012 |
| EM | 0013233070012 | 4/2012 |
| EM | 0024296960003 | 3/2014 |
| EM | 0024296960004 | 3/2014 |
| EM | 0014157800001 | 7/2014 |
| EM | 0014157800002 | 7/2014 |
| EM | 0014157800003 | 7/2014 |
| EM | 0014157800004 | 7/2014 |
| EM | 0014157800005 | 7/2014 |
| EM | 0014157800006 | 7/2014 |
| EM | 0014157800007 | 7/2014 |
| EM | 0014157800008 | 7/2014 |
| EM | 0014157800009 | 7/2014 |
| EM | 0026967650003 | 5/2015 |
| EM | 0029228640002 | 12/2015 |
| EP | 1496858 A1 | 1/2005 |
| EP | 2319334 A1 | 5/2011 |
| EP | 2460424 A1 | 6/2012 |
| EP | 1496858 B1 | 8/2013 |
| EP | 2801270 A2 | 11/2014 |
| EP | 2875740 A2 | 5/2015 |
| EP | 2878213 A1 | 6/2015 |
| EP | 3039976 A1 | 7/2016 |
| EP | 3292775 A1 | 3/2018 |
| FR | 970852009 | 8/1997 |
| FR | 983203001 | 10/1998 |
| FR | 956833001 | 1/1999 |
| FR | 001967001 | 7/2000 |
| FR | 007595001 | 4/2001 |
| FR | 007595002 | 4/2001 |
| FR | 011038001 | 5/2001 |
| FR | 011152001 | 5/2001 |
| FR | 011154001 | 5/2001 |
| FR | 201125490001 | 7/2011 |
| FR | 201127120001 | 7/2011 |
| FR | 201127120002 | 7/2011 |
| FR | 201127120003 | 7/2011 |
| FR | 2962339 A1 | 1/2012 |
| FR | 20124875012 | 8/2013 |
| FR | 3039039 A1 | 1/2017 |
| GB | 488340 A | 7/1938 |
| GB | 911405 A | 11/1962 |
| GB | 2047060 A | 11/1980 |
| GB | 2115679 A | 9/1983 |
| GB | 1029228 | 4/1986 |
| GB | 2191718 A | 12/1987 |
| GB | 2048538 | 11/1995 |
| GB | 2055446 | 8/1996 |
| GB | 2075058 | 9/1998 |
| GB | 2093858 | 8/2000 |
| GB | 2093859 | 8/2000 |
| GB | 2412876 A | 10/2005 |
| GB | 4020185 | 11/2011 |
| GB | 2504077 A | 1/2014 |
| GB | 2508520 A | 6/2014 |
| GB | 2515562 A | 12/2014 |
| GB | 4041108 | 6/2015 |
| IT | 1993MIO0001280003 | 3/1993 |
| IT | 2000TOO0002350001 | 9/2000 |
| IT | 2000TOO0002350003 | 9/2000 |
| IT | 2000TOO0002350004 | 9/2000 |
| IT | 2000TOO0002350006 | 9/2000 |
| IT | 2002TOO0002140001 | 9/2002 |
| IT | 2002TOO0002140002 | 9/2002 |

(56) References Cited

FOREIGN PATENT DOCUMENTS

| | | |
|---|---|---|
| IT | 2002TOO0002140003 | 9/2002 |
| IT | 2002TOO0002140004 | 9/2002 |
| JP | H0712849 Y2 | 3/1995 |
| JP | H08322934 A | 12/1996 |
| JP | H08511966 A | 12/1996 |
| JP | 2005525393 A | 8/2005 |
| JP | 2007501271 A | 1/2007 |
| JP | 2007502683 A | 2/2007 |
| JP | 2007511437 A | 5/2007 |
| JP | 2009536062 A | 10/2009 |
| JP | 2013507976 A | 3/2013 |
| JP | 2013545473 A | 12/2013 |
| JP | 2014519850 A | 8/2014 |
| JP | 2014237011 A | 12/2014 |
| JP | 2015504653 A | 2/2015 |
| JP | 2015526266 A | 9/2015 |
| JP | D1575098 S | 3/2017 |
| JP | 2017522873 A | 8/2017 |
| JP | 6621154 B2 | 12/2019 |
| KR | 100495099 B1 | 11/2005 |
| KR | 20120098343 A | 9/2012 |
| KR | 101256914 B1 | 4/2013 |
| KR | 20150036557 A | 4/2015 |
| KZ | 30993 B | 3/2016 |
| RU | 115629 U1 | 5/2012 |
| RU | 122000 U1 | 11/2012 |
| RU | 2536032 C2 | 12/2014 |
| RU | 2698528 C1 | 8/2019 |
| UA | 109556 C2 | 9/2015 |
| WO | WO-DM264451 | 6/1993 |
| WO | WO-DM0264451 | 6/1996 |
| WO | WO-9912596 A1 | 3/1999 |
| WO | WO-0205881 A1 | 1/2002 |
| WO | WO-03095005 A1 | 11/2003 |
| WO | WO-2007007110 A1 | 1/2007 |
| WO | WO-2009092520 A1 | 7/2009 |
| WO | WO-2009092653 A1 | 7/2009 |
| WO | WO-2010114504 A1 | 10/2010 |
| WO | WO-2012004512 A1 | 1/2012 |
| WO | WO-2012004514 A1 | 1/2012 |
| WO | WO-2012004518 A1 | 1/2012 |
| WO | WO-2012010878 A1 | 1/2012 |
| WO | WO-2012047181 A1 | 4/2012 |
| WO | WO-2013083638 A1 | 6/2013 |
| WO | WO-2013118299 A1 | 8/2013 |
| WO | WO-2014066730 A1 | 5/2014 |
| WO | WO-2014135224 A1 | 9/2014 |
| WO | WO-2014159250 A1 | 10/2014 |
| WO | WO-2014201432 A1 | 12/2014 |
| WO | WO-2014204417 A1 | 12/2014 |
| WO | WO-2015006838 A1 | 1/2015 |
| WO | WO-2015022436 A1 | 2/2015 |
| WO | WO-2015073564 A1 | 5/2015 |
| WO | WO-2015112750 A1 | 7/2015 |
| WO | WO-2015113743 A1 | 8/2015 |
| WO | WO-2015117700 A1 | 8/2015 |
| WO | WO-2015166239 A1 | 11/2015 |
| WO | WO-2015173303 A1 | 11/2015 |
| WO | WO-2015175568 A1 | 11/2015 |
| WO | WO-2016005600 A1 | 1/2016 |
| WO | WO-2016014652 A1 | 1/2016 |
| WO | WO-2016079410 A1 | 5/2016 |
| WO | WO-2016107764 A2 | 7/2016 |
| WO | WO-2016107767 A1 | 7/2016 |
| WO | WO-2016118005 A1 | 7/2016 |
| WO | WO-2016122417 A1 | 8/2016 |
| WO | WO-2016150019 A1 | 9/2016 |
| WO | WO-2016159919 A1 | 10/2016 |
| WO | WO-2017011865 A1 | 1/2017 |
| WO | WO-2017013130 A1 | 1/2017 |
| WO | WO-DM094223001 | 1/2017 |
| WO | WO-2017024799 A1 | 2/2017 |
| WO | WO-2017163044 A1 | 9/2017 |
| WO | WO-2017163045 A1 | 9/2017 |
| WO | WO-2017163050 A1 | 9/2017 |
| WO | WO-2017163051 A1 | 9/2017 |
| WO | WO-2017163052 A1 | 9/2017 |
| WO | WO-2017206211 A1 | 12/2017 |

OTHER PUBLICATIONS

Decision to Grant dated Mar. 27, 2019 for Russian Application No. 2018133622, 14 pages.
Decision to Grant dated May 30, 2019 for Russian Application No. 2018132701, 14 pages.
Decision to Grant dated Aug. 28, 2017 for Russian Application No. 201750018449, 4 pages.
Electronic Cigarette | Vype Pebble | Govype, post date n/a, (c)n/a, govype.com, Aug. 30, 2017, https://www.govype.com/uk/vype-pebble-starter-kit. cited by examiner, 2 pages.
Examination Report for Canadian Application No. 169756, dated Nov. 17, 2016, 1 page.
Formalities Notice No. 1 for Australian Design Application No. AU201614224, dated Aug. 9, 2016., 2 pages.
Formalities Notice No. 1 for Australian Design Application No. 201614225, dated Aug. 9, 2016, 2 pages.
Innokin EQ Pod System Vape Kit by vapeclub. dated 2018. found online [Sep. 24, 2018] https://www.vapeclub.co.uk/pods-and-closed-system-vape-starter- kits/innokin-eq-pod-system-vape-kit.html, 6 pages.
International Preliminary Report on Patentability for Application No. PCT/GB2017/050787, dated Feb. 27, 2018, 12 pages.
International Search Report and Written Opinion for Application No. PCT/GB2017/050787, dated Jul. 3, 2017, 12 pages.
International Preliminary Report on Patentability for Application No. PCT/GB2017/050783, dated Jul. 6, 2018, 13 pages.
International Search Report and Written Opinion for Application No. PCT/GB2017/050783, dated Jun. 9, 2017, 15 pages.
International Preliminary Examining Authority for Application No. PCT/GB2017/050783, dated Jun. 12, 2018, 6 pages.
International Preliminary Reporton Patentability for Application No. PCT/GB2017/050781, dated Feb. 27, 2018, 13 pages.
International Preliminary Report on Patentability for Application No. PCT/GB2017/050788, dated Aug. 3, 2018, 14 pages.
International Preliminary Report on Patentability for Application No. PCT/GB2017/050789, dated Jul. 11, 2018, 13 pages.
International Search Report and Written Opinion for Application No. PCT/GB2017/050781 dated Jun. 14, 2017.
International Search Report and Written Opinion for Application No. PCT/GB2017/050788, dated Jun. 7, 2017, 13 pages.
International Search Report and Written Opinion for Application No. PCT/GB2017/050789, dated Jun. 7, 2017, 9 pages.
International Second Written Opinion for PCT Application No. PCT/GB2017/050788, dated Mar. 7, 2018, 9 pages.
JustFog C601 Pod System Vape Kit by vapeclub. dated 2018. found online [Sep. 24, 2018] https://www.vapeclub.co.uk/pods-and-closed-system-vape-starter-kits/justfog-c601-pod-system-vape-kit.html, 6 pages.
Notice of Allowance for Chinese Application No. 201630632827.4, dated Feb. 24, 2017, 2 pages.
Notice of Allowance for Japanese Application No. 2016016955, dated Feb. 14, 2017, 2 pages.
Notice of Allowance for Japanese Application No. 2016016956, dated Feb. 14, 2017, 2 pages.
Notice of Allowance for Japanese Application No. 2017-000313, dated Dec. 19, 2017, 3 pages.
Notice of Issuance for Chinese Application No. 201630370608.3, dated Dec. 30, 2016, 3 pages.
Notice of Reason for Refusal for Japanese Application No. 2018-548027 dated Dec. 10, 2019, 10 pages.
Notice of Reason for Refusal for Japanese Application No. 2018-548374 dated Oct. 1, 2019, 8 pages.
Office Action dated Jun. 1, 2020 for Chinese Application No. 201780019532.1, 46 pages.
Office Action dated Feb. 2, 2021 for Ukraine Application No. 201809441, 11 pages.
Office Action dated May 20, 2020 for Chinese Application No. 201780018952.8, 21 pages.

(56) References Cited

OTHER PUBLICATIONS

Office Action for Canadian Application No. 3,018,460, dated Jul. 23, 2019, 6 pages.
Office Action for Chinese Application No. 201630370608.3, dated Nov. 1, 2016, 1 page.
Office Action for Japanese Application No. 2017-000313, dated Aug. 29, 2017, 4 pages.
Office Action dated Oct. 14, 2019 for Chilean Application No. 201802657, 16 pages.
Office Action dated Feb. 17, 2020 for Chilean Application No. 201802640, 15 pages.
Office Action dated Oct. 17, 2019 for Korean Application No. 10-2018-7038106, 17 pages.
Office action dated May 26, 2020 for Japanese Application No. 2018-545821, 8 pages.
Office Action dated Jun. 29, 2020 for Chinese Application No. 201780018542.3, 12 pages.
Office Action dated Mar. 30, 2020 for Korean Application No. 10-2018-7027563, 21 pages.
Office Action dated Feb. 21, 2017 for Russian Application No. 2016505393.
Office Action dated Jan. 13, 2017 for Ukrainian Application No. S201601341, 1 pages.
Office Action dated Nov. 23, 2016 for Mexican Application No. MX/f/2016/002430, 1 pages.
Office Action dated Oct. 6, 2016 for Russian Application No. 2016503052, 2 pages.
Search Report dated Jun. 10, 2019 for Russian Application No. 2018133541, 2 pages.
Search Report dated Aug. 11, 2016 for Great Britain Application No. 1605104.7, 5 pages.
Search Report dated Aug. 16, 2016 for Great Britain Application No. 1605103.9, 4 pages.
Search Report dated Aug. 25, 2016 for Great Britain Application No. 1605100.5, 3 pages.
Search Report dated Aug. 3, 2016 for Great Britain Application 1605106.2, 5 pages.
Search Report dated Feb. 9, 2016 for Great Britain Application No. GB1517088.9, 3 pages.
Search Report dated Jun. 9, 2017 for Great Britain Application No. 1612684.9, 4 pages.
Smoant S8 Ultra-Portable System Kit _ Premium Electronic Cigarette by wicked vapor, mailed 2018, found online on Sep. 24, 2018, at https://wicked-vapor.com/products/smoant-s8-ultra-portable-system-kit, 2 pages.
U.S. Appl. No. 16/086,997, filed Sep. 20, 2018, Nettenstrom et al., Inventor(s), 43 pages.
U.S. Appl. No. 16/087,005, filed Sep. 20, 2018, Nettenstrom et al., Inventor(s), 37 pages.
U.S. Appl. No. 16/087,012, filed Sep. 20, 2018, Nettenstrom et al., Inventor(s), 39 pages.
U.S. Appl. No. 16/087,021, filed Sep. 20, 2018, Nettenstrom et al., Inventor(s), 27 pages.
Vincent V., "Renova Vapor Zero vape Pod Kit", mailed May 29, 2018, found online on Sep. 24, 2018, https://www.e-cigarette-forum.com/threads/renova-vapor-zero-vape-pod-kit-hqd-comma-vape-pod-kit-wismec-hiflask-pod-kit.865421/.
Written Opinion of the International Preliminary Examining Authority for Application No. PCT/GB2017/050783, dated Mar. 2, 2018, 6 pages.
Decision fro Korean Application No. 3020160038357_M002 dated Dec. 14, 2016., 3 pages.
Decision to Grant a Patent dated Oct. 23, 2019 for Japanese Application No. 2018-545824, 5 pages.
Decision to Grant dated Aug. 15, 2017 for Russian Application No. 201650539349, 4 pages.
Office Action For GB Application No. 1605104.7, dated Apr. 12, 2021, 6 pages.
Office Action For Korean Application No. 2018-7027488, dated Jul. 22, 2021, 20 pages.
Search Report fro Japanese Application No. 2018-548374, dated Sep. 25, 2019, 35 pages.
Search Report dated Nov. 25, 2019 for Japanese Application No. 2018-548027, 26 pages.
Search Report dated Sep. 5, 2019 for Japanese Application No. 2018-545821, 41 pages.

* cited by examiner

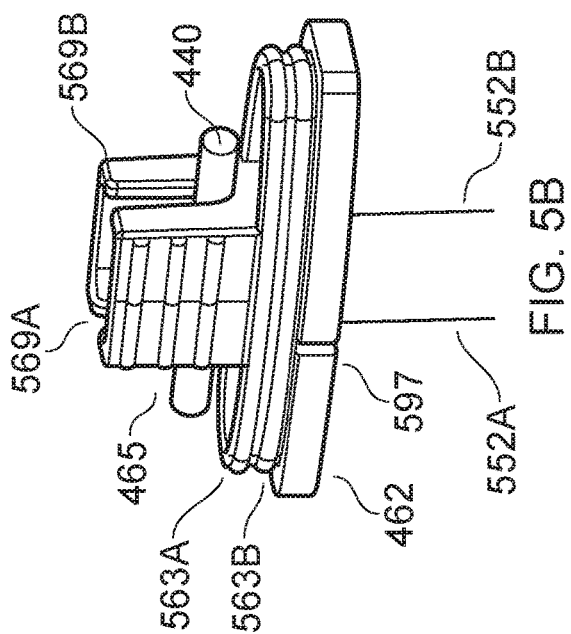
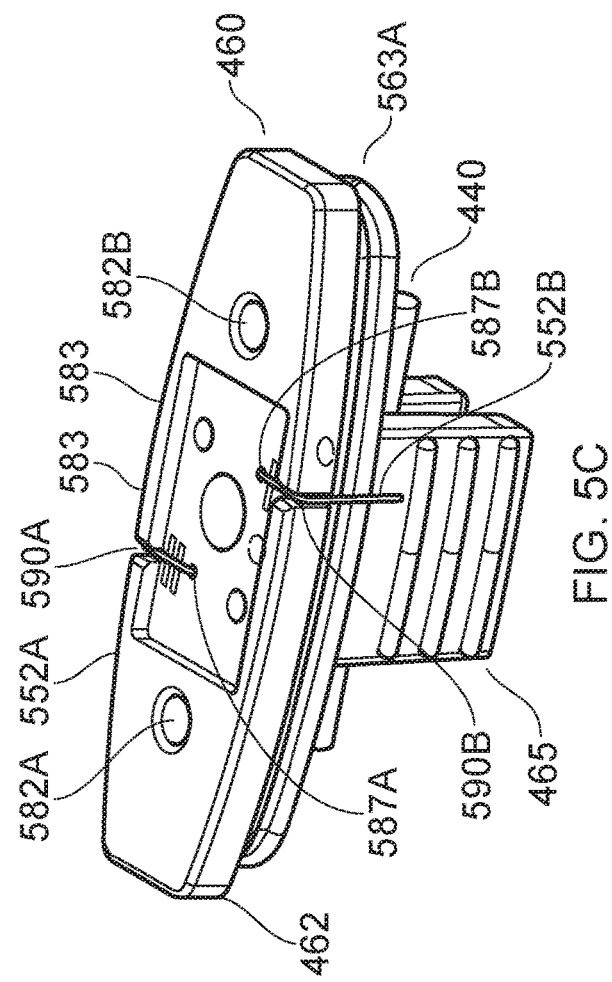
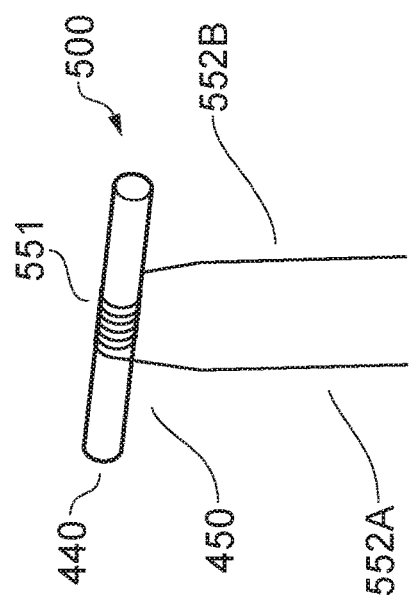

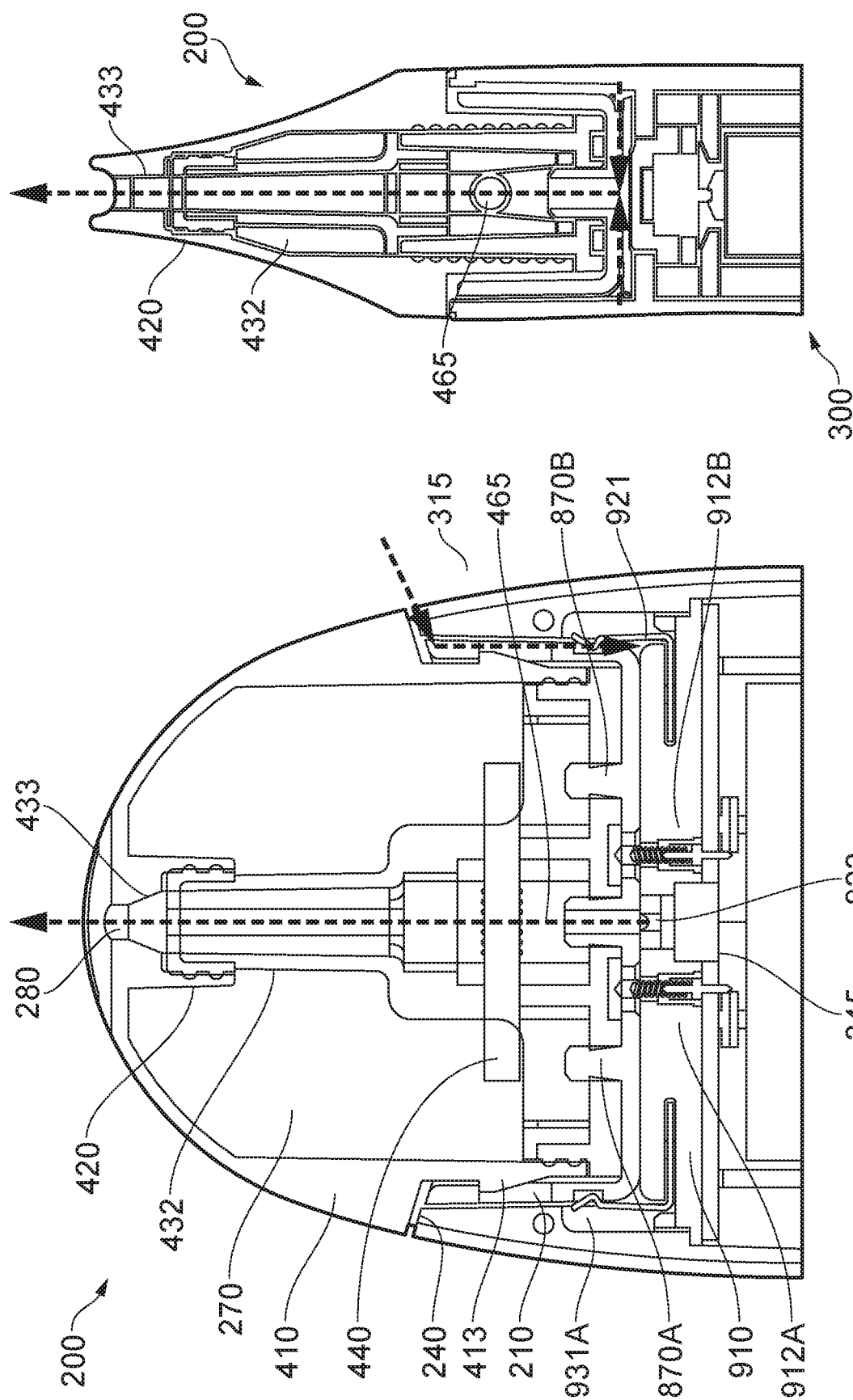

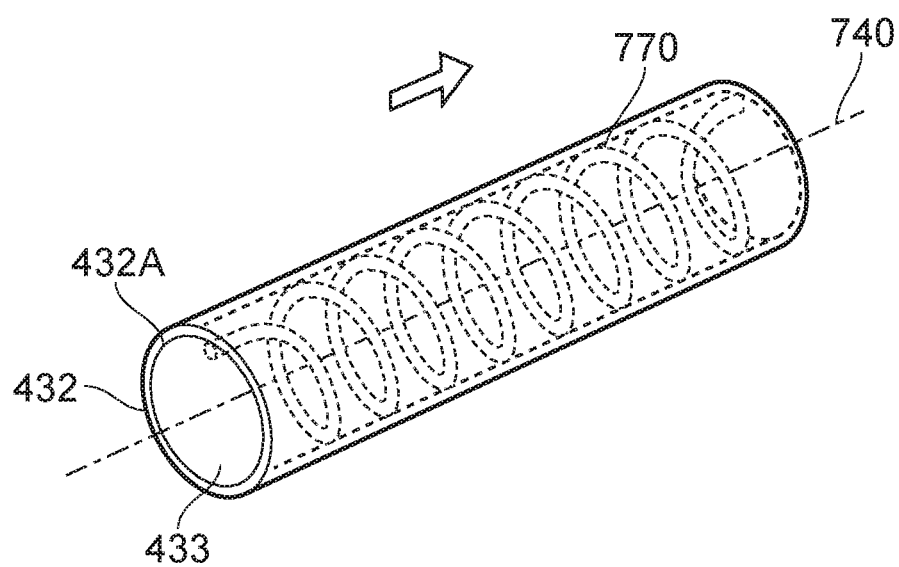
FIG. 13A
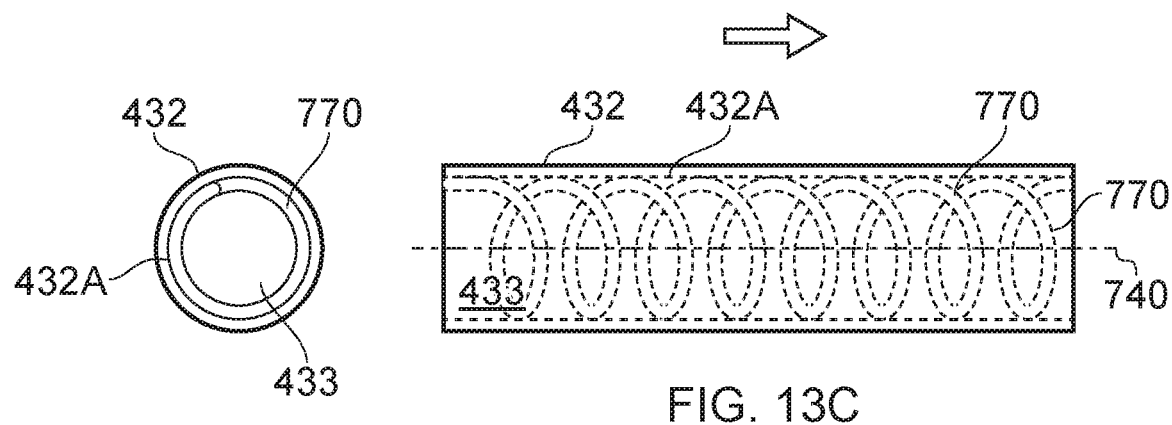
FIG. 13B
FIG. 13C

VAPOR PROVISION APPARATUS

PRIORITY CLAIM

The present application is a National Phase entry of PCT Application No. PCT/GB2017/050783, filed Mar. 21, 2017, which claims priority from GB Patent Application No. 1605105.4, filed Mar. 24, 2016, which is hereby fully incorporated herein by reference.

FIELD

The present disclosure relates to vapor provision systems such as nicotine delivery systems (e.g. electronic cigarettes and the like), and detachable cartridges/cartomizers for use in such systems, and more particularly to airflows in vapor provision systems.

BACKGROUND

Electronic vapor provision systems such as electronic cigarettes (e-cigarettes) generally contain a vapor precursor material, such as a reservoir of a source liquid containing a formulation, typically including nicotine, or a solid material such a tobacco-based product, from which a vapor is generated for inhalation by a user, for example through heat vaporization. Thus, a vapor provision system will typically comprise a vapor generation chamber containing a vaporizer, e.g. a heating element, arranged to vaporize a portion of precursor material to generate a vapor in the vapor generation chamber. As a user inhales on the device and electrical power is supplied to the vaporizer, air is drawn into the device through inlet holes and into the vapor generation chamber where the air mixes with the vaporized precursor material. There is a flow path connecting between the vapor generation chamber and an opening in the mouthpiece so the incoming air drawn through the vapor generation chamber continues along the flow path to the mouthpiece opening, carrying some of the vapor with it, and out through the mouthpiece opening for inhalation by the user.

User experiences with electronic vapor provision systems are continually improving as such systems become more refined in respect of the nature of the vapor they provide for user inhalation, for example in terms of deep lung delivery, mouth feel and consistency in performance. Nonetheless, approaches for improving further still on these aspects of electronic vapor provision systems remain of interest.

SUMMARY

According to a first aspect of certain embodiments there is provided a vapor provision apparatus comprising: a vapor generation chamber containing a vaporizer for generating vapor from a vapor precursor material; and an air channel wall defining an air channel between the vapor generation chamber and a vapor outlet at a mouthpiece end of the vapor provision apparatus through which a user can inhale vapor during use; wherein an inner surface of the air channel wall is provided with at least one protrusion extending into the air channel to modify a flow of air in the air channel during use.

According to another aspect there is provided vapor provision means comprising: vapor generation chamber means containing vapor generation means for generating a vapor from vapor precursor material means; and air channel wall means defining air channel means fluidly connecting between the vapor generation chamber means and vapor outlet means at a mouthpiece end of the vapor provision means through which a user can inhale vapor during use; wherein an inner surface of the air channel wall means is provided with protrusion means extending into the air channel means for modifying a flow of air in the air channel means during use.

These and further aspects of certain embodiments are set out in the appended independent and dependent claims. It will be appreciated that features of the dependent claims may be combined with each other and features of the independent claims in combinations other than those explicitly set out in the claims. Furthermore, the approaches described herein are not restricted to specific embodiments such as the examples set out below, but include and contemplate any appropriate combinations of features presented herein. For example, a vapor provision system may be provided in accordance with approaches described herein which includes any one or more of the various features described below as appropriate.

BRIEF DESCRIPTION OF THE DRAWINGS

FIGS. 5A, 5B and 5C illustrate the wick/heater assembly being fitted into the cartomizer plug in accordance with some embodiments of the disclosure.

FIGS. 10A and 10B are cross-sections respectively (a) from side to side, and (b) from front to back, showing the airflow through the e-cigarette of FIG. 1 in accordance with some embodiments of the disclosure.

FIGS. 11A, 11B, 11C, 12A, 12B, 13A, 13B, 13C, 14A, and 14B are schematic views of various aspects of air channels in accordance with some embodiments of the disclosure.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to aerosol provision systems, also referred to as vapor provision systems, such as e-cigarettes. Throughout the following description the term "e-cigarette" or "electronic cigarette" may sometimes be used; however, it will be appreciated this term may be used interchangeably with aerosol (vapor) provision system and electronic aerosol (vapor) provision system.

Figure 1:
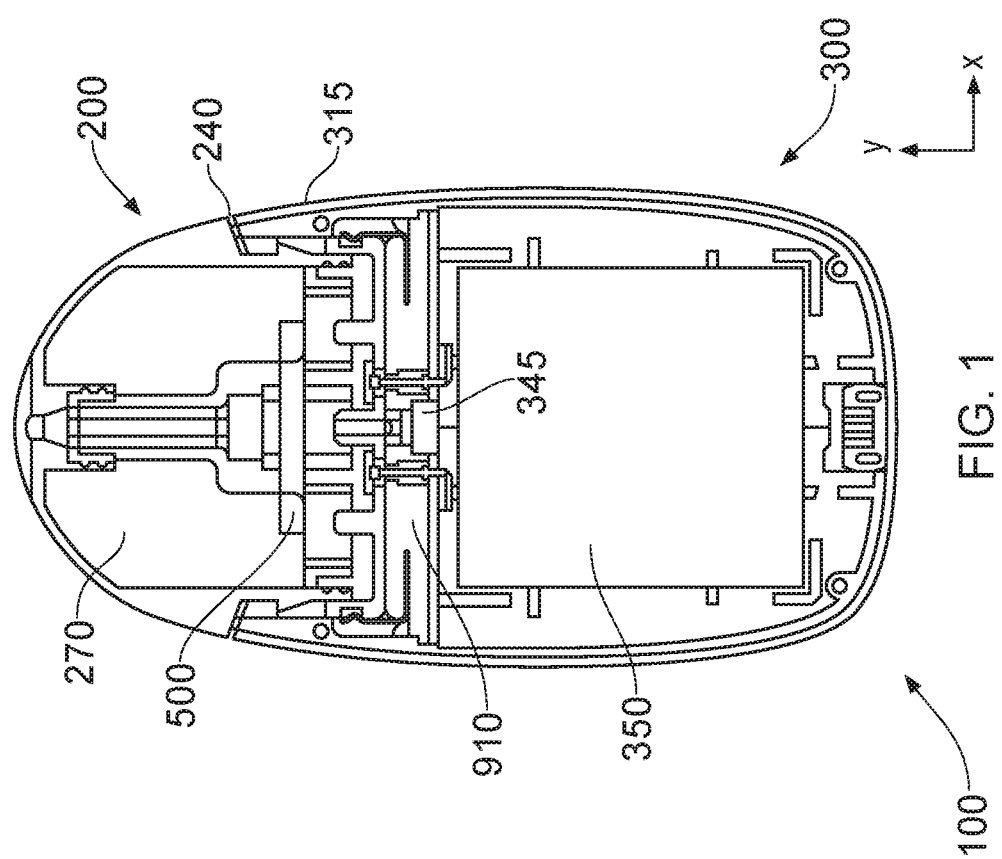
FIG. 1 is a cross-section through an e-cigarette comprising a cartomizer and a control unit in accordance with some embodiments of the disclosure.

FIG. 1 is a cross-sectional view through an example e-cigarette 100 (i.e. an example of a vapor provision system) in accordance with some embodiments of the disclosure. The e-cigarette 100 comprises two main components which are separable from one another, namely a cartomizer 200 and a control unit 300.

As discussed in more detail below, cartomizer includes a chamber 270 containing a reservoir of liquid, a heater to act as an atomizer or vaporizer, and a mouthpiece. The liquid in the reservoir (sometimes referred to as the e-liquid) typically includes nicotine in an appropriate solvent, and may include further constituents, for example, to aid aerosol formation, and/or for additional flavoring. The cartomizer 200 further includes a wick/heater assembly 500, which includes a wick or similar facility to transport a small amount of liquid from the reservoir 270 to a heating location on or adjacent the heater. The control unit 300 includes a re-chargeable cell or battery 350 to provide power to the e-cigarette 100, a printed circuit board (PCB) for generally controlling the e-cigarette 100 (not shown in FIG. 1), and a microphone 345 for detecting a user inhalation (via a pressure drop). When the heater receives power from the battery 350, as controlled by the PCB in response to the microphone 345 detecting a user puff on the e-cigarette 100, the heater vaporizes the liquid from the wick and this vapor is then inhaled by a user through the mouthpiece.

For ease of reference, x- and y-axes are marked in FIG. 1. The x-axis will be referred to herein as the width of the device 100 (from side to side as shown in FIG. 1), while the y-axis (from bottom to top as shown in FIG. 1) will be referred to herein as the height axis, where the cartomizer 200 represents an upper portion of the e-cigarette 100 and the control unit 300 represents a lower portion of the e-cigarette 100. Note that this orientation reflects how a user might hold the e-cigarette 100 during normal operation of the device 100, for example between puffs, given that the wick is located in the lower part of the reservoir 270 in the cartomizer 200. Therefore holding the e-cigarette 100 in this orientation can help ensure the wick is in contact with liquid at the bottom of the liquid reservoir 270.

We further assume a z-axis (not shown in FIG. 1) is perpendicular to the x- and y-axes shown in FIG. 1. The z-axis will be referred to herein as the depth axis. The depth of the e-cigarette 100 in this example is significantly less than the width of the e-cigarette 100, thereby resulting in a generally flat or planar configuration (in the x-y plane). Accordingly, the z-axis can be considered as extending from face to face of the e-cigarette 100, where one face may be regarded (arbitrarily) as the front face of the e-cigarette 100 and the opposing face as the back face of the e-cigarette 100. However, it will be appreciated the principles described herein may also be applied to electronic cigarettes having generally different shapes and sizes.

The cartomizer 200 and the control unit 300 are detachable from one another by separating in a direction parallel to the y-axis, but are joined together when the device 100 is in use so as to provide mechanical and electrical connectivity between the cartomizer 200 and the control unit 300. When the e-liquid in the cartomizer reservoir 270 has been depleted, or the user wishes to switch to a different cartomizer, for example containing a different flavor vapor precursor material, the cartomizer 200 is removed and a new cartomizer is attached to the control unit 300. Accordingly, the cartomizer 200 may sometimes be referred to as a disposable portion of the e-cigarette 100, while the control unit 300 represents a re-usable portion. Alternatively, the cartomizer 200 may be configured to be refillable with e-liquid, and may in some cases require detachment from the control unit 300 for access to a filling port.

Figure 2:
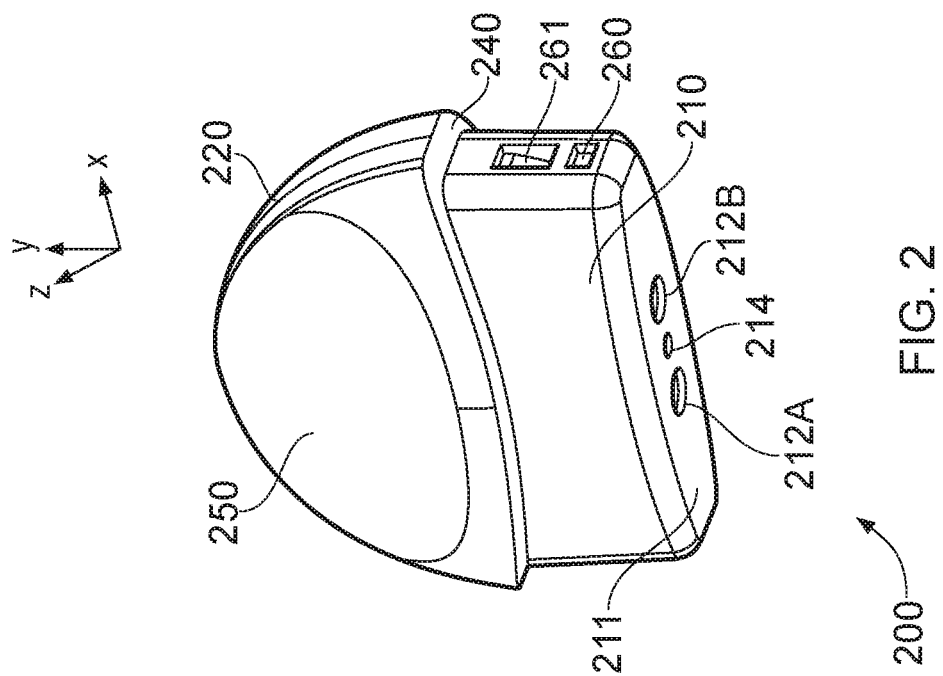
FIG. 2 is an isometric external view of the cartomizer of the e-cigarette of FIG. 1 in accordance with some embodiments of the disclosure.

FIG. 2 is an isometric external view of the cartomizer 200 of the e-cigarette 100 of FIG. 1 in accordance with some embodiments of the disclosure. The orientation relative to the view of FIG. 1 is apparent from the representation of the xyz-axes. This external view demonstrates the depth of the cartomizer 200 (as for the e-cigarette 100 as a whole) measured parallel to the z-axis, is somewhat less than the width of the cartomizer 200 (and the e-cigarette 100 as a whole) measured parallel to the x-axis in this specific example. However, as already noted above, the principles described herein are equally applicable for other sizes and shapes of vapor provision systems, for example including vapor provision systems of more conventional shapes, such as generally cylindrical systems or box-based systems.

The cartomizer 200 may, at least from an external viewpoint, be considered to comprise two main portions. In particular, there is a lower or base portion 210 and an upper portion 220 (the terms upper and lower are used here with reference to the orientation shown in FIG. 1). When the cartomizer 200 is assembled with the control unit 300, the base portion 210 of the cartomizer 200 sits within the control unit 300, and hence is not externally visible, whereas the upper portion 220 of the cartomizer 200 protrudes above the control unit 300, and hence is externally visible. Accordingly, the depth and width of the base portion 210 are smaller than the depth and width of the upper portion 220, to allow the base portion to fit within the control unit 300. The increase in depth and width of the upper portion 220 compared with the base portion 210 is provided by a lip or rim 240. When the cartomizer 200 is inserted into the control unit 300, this lip or rim 240 abuts against the top of the control unit 300.

As shown in FIG. 2, the side wall of base portion 210 includes a notch or indentation 260 for receiving a corresponding latching member from the control unit 300. The opposite side wall of the base portion 210 is provided with a similar notch or indentation to likewise receive a corresponding latching member from the control unit 300. It will be appreciated that this pair of notches 260 on the base portion 200 (and the corresponding latching members of the control unit 300) provide a latch or snap fit connection for securely retaining the cartomizer 200 within the control unit 300 during operation of the device 100. Adjacent to the notch 260 is a further notch or indentation 261, which is utilized in the formation of the cartomizer 200.

As also shown in FIG. 2, the bottom wall 211 of the base portion 210 includes two larger holes 212A, 212B on either side of a smaller hole 214 for air inlet. The larger holes 212A and 212B are used to provide positive and negative electrical connections from the control unit 300 to the cartomizer 200. Thus when a user inhales through the mouthpiece 250 and the device 100 is activated, airflows into the cartomizer 200 through the air inlet hole 214. This incoming airflows past the heater (not visible in FIG. 2), which receives electrical power from the battery 350 in the control unit 300 so as to vaporize liquid from the reservoir 270 (and more especially from the wick). This vaporized liquid is then incorporated or entrained into the airflow through the cartomizer 200, and hence is drawn out of the cartomizer 200 through mouthpiece 250 for inhalation by the user.

Figure 3:
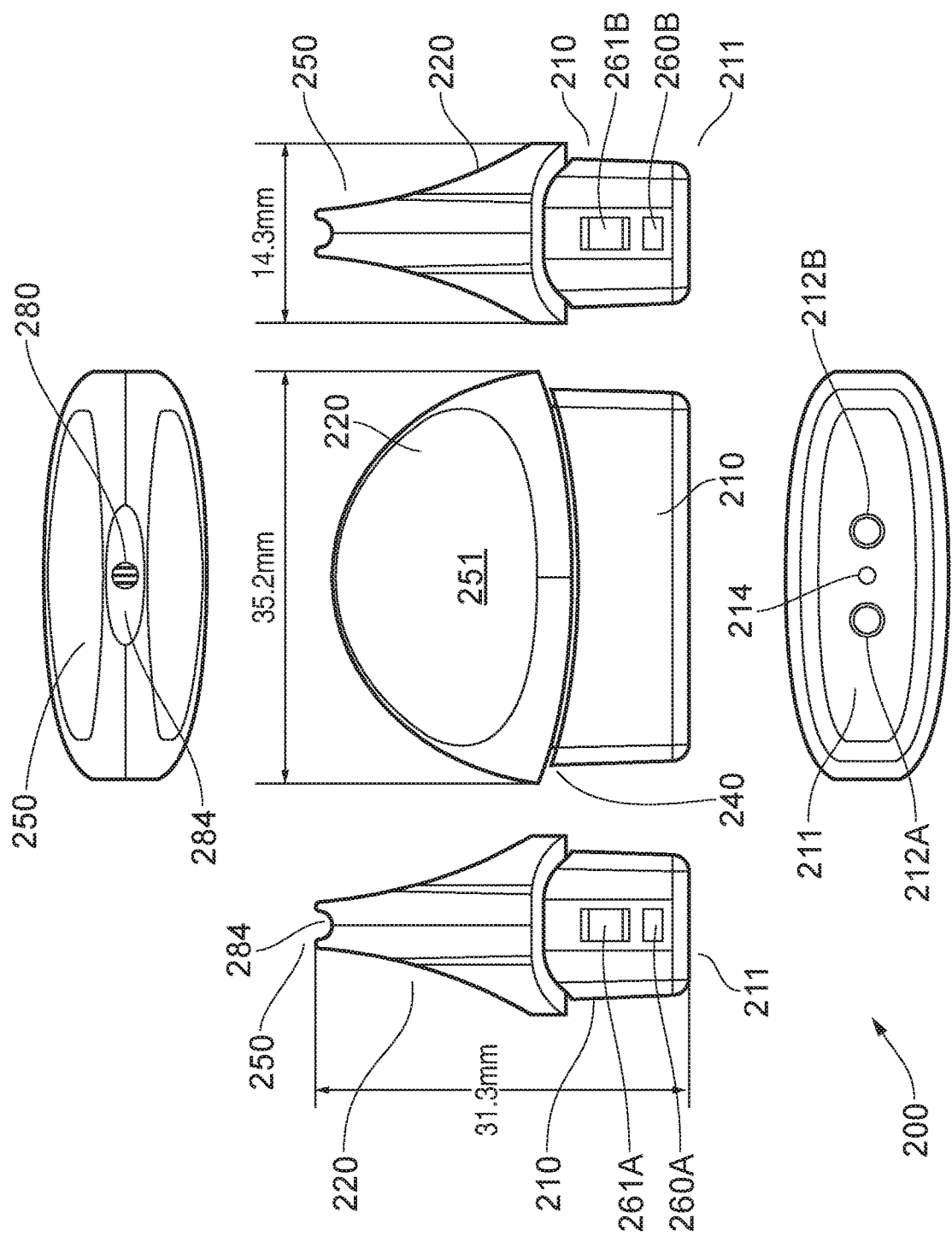
FIG. 3 is a collection of five external views of the cartomizer of FIG. 2 in accordance with some embodiments of the disclosure. In particular, the bottom view shows the cartomizer from underneath, the top view shows the cartomizer from above, the central view shows a face view of the cartomizer (from front or back), and on either side of the central view are respective side views of the cartomizer.

FIG. 3 is a collection of five external views of the cartomizer 200 of FIG. 2 in accordance with some embodiments of the disclosure. In particular, the bottom view shows the cartomizer 200 from underneath (with reference to the orientation of FIG. 1), the top view shows the cartomizer 200 from above, the central view shows a face view of the cartomizer 200 (from front or back), and on either side of the central view are respective side views of the cartomizer 200. Note that since the cartomizer 200 is symmetric front/back (i.e. with respect to the z-axis), the front face of the cartomizer 200 and the back face of the cartomizer 200 both correspond to the central view of FIG. 3. In addition, the cartomizer 200 is also symmetric in the width direction (i.e. with respect to the x-axis), hence the two side views to the left and right of the central view appear the same.

FIG. 3 illustrates the various features of the cartomizer 200 already discussed above with respect to FIG. 2. For example, the central view clearly shows the top portion 220 and the bottom portion 210 of the cartomizer 200. The lower view shows the bottom wall of the base portion 211, including the two larger holes 212A and 212B, which are used to provide positive and negative electrical connections from the control unit 300 to the cartomizer 200, plus the smaller hole 214 for air inlet into the cartomizer. In addition, the two side views show the two notches in each side wall, an upper notch 261A, 261B, and a lower notch 260A, 260B, the latter being used to fasten the cartomizer 200 to the control unit 300.

The top view further shows a hole 280 in the mouthpiece 250 which represents the air/vapor outlet from the cartomizer 200. Thus in operation, when a user inhales, air enters the cartomizer 200 at the bottom through inlet 214, flows through the atomizer, including past the heater, where it acquires vapor, and then travels up the center of the cartomizer 200 to exit through air outlet 280.

For the sake of providing a concrete example, FIG. 3 provides exemplary dimensions for the cartomizer 200, showing a largest height (in the y-direction) of around 31.3 mm, a largest width (in the x-direction) of around 35.2 mm, and a largest depth of around 14.3 mm (parallel to the z-direction). Note that these largest width and depth measurements relate to the upper portion 220 of the cartomizer 200; the width and depth of the base portion 210 are somewhat smaller, in order to allow the base portion 210 to be received into the control unit 300. The difference in width and depth between the upper portion 220 and the base portion 210 is accommodated by the rim or flange 240, as described above.

FIG. 3 also gives an indication of the size and shape of the mouthpiece 250. In contrast to many e-cigarettes, which provide a circular mouthpiece akin to a straw or conventional cigarette, the mouthpiece 250 in this example has a different overall shape. In particular, the mouthpiece 250 comprises a pair of large, relatively flat, opposing faces. One of these mouthpiece faces is denoted as face 251 in the central view of FIG. 3, and there is a corresponding, opposing face to the rear of the device. (Note that the labeling of front and back for the cartomizer 200 is arbitrary, since it is symmetric with respect to the z-axis, and can be fitted either way around onto the control unit 300.) Nonetheless, as already mentioned the principles described herein can be implemented in devices of different overall shape and size.

As can be seen in FIG. 3, the front and back faces 251 do not converge completely at the top of the mouthpiece 250, but rather overhang to provide a small valley 284 which extends in the x-direction of the device. The opening 280, which allows air and vapor to exit from the cartomizer 200, is formed in the center of this valley 284. Having this small overhang, so that the mouthpiece opening 280 is located in the groove or valley 284, helps to protect the mouthpiece opening 280 from physical contact, and hence from potential damage and dirt.

Figure 4:
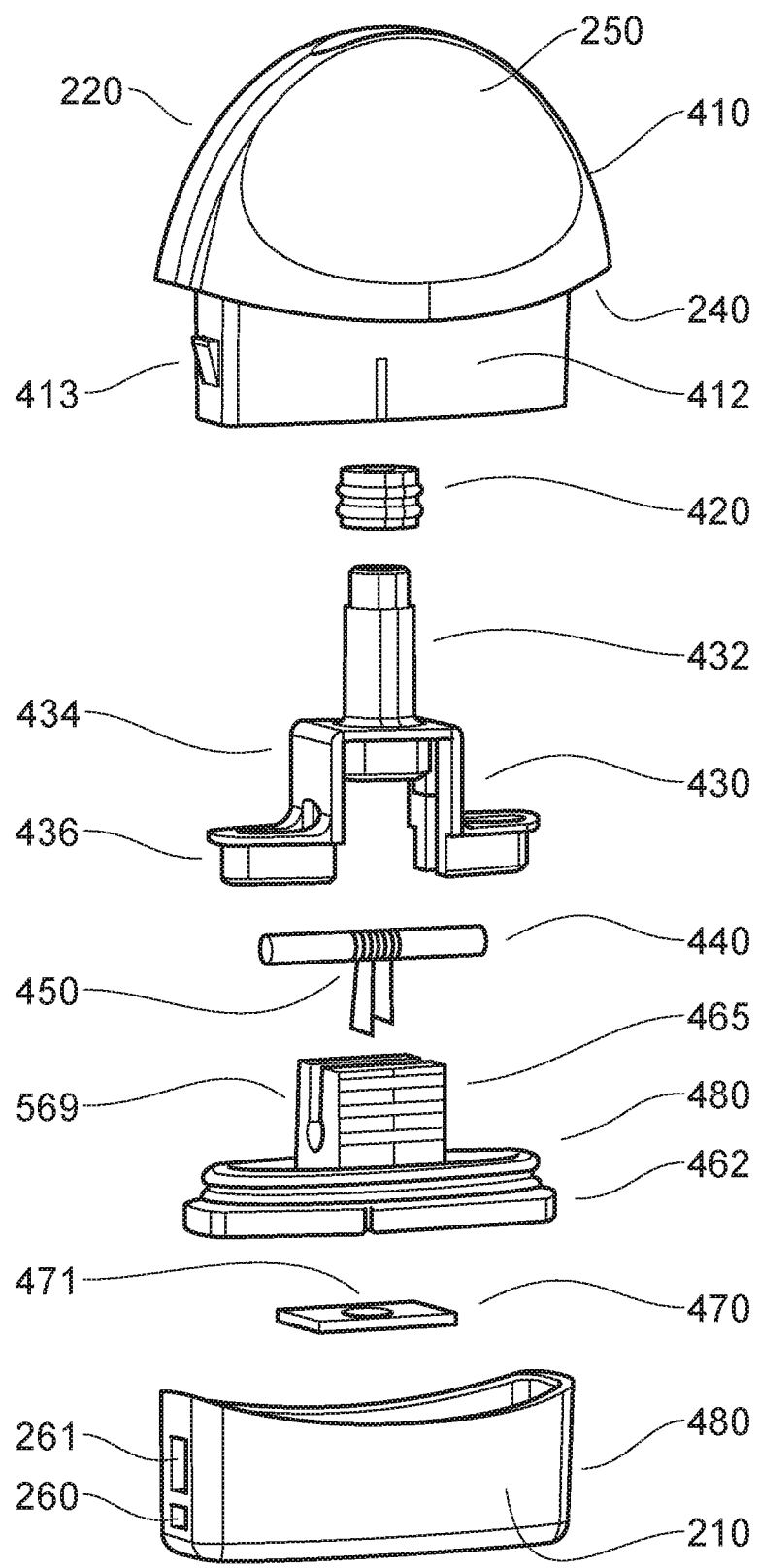
FIG. 4 is an exploded view of the cartomizer of the e-cigarette of FIG. 1 in accordance with some embodiments of the disclosure.

FIG. 4 is an exploded view of the cartomizer 200 of the e-cigarette 100 of FIG. 1 in accordance with some embodiments of the disclosure. The cartomizer 200 includes a shell 410, a vent seal 420, an inner frame 430, a heating coil 450 located on a wick 440, a primary seal 460 (also referred to as the cartomizer plug), a printed circuit board (PCB) 470 and an end cap 480. The view of FIG. 4 shows the above components exploded along the longitudinal (height or y) axis of the cartomizer 200.

The cap 480 is formed from substantially rigid plastic such as polypropylene and provides the base portion 210 of the cartomizer 200. The cap 480 is provided with two holes 260, 261 on each side (only one side is visible in FIG. 4, but the side which is not visible is the same as the side that is visible). The lower hole 260 is for latching the cartomizer 200 to the control unit 300, while the upper hole 261 is for latching the end cap 480 to the shell 410. As described in more detail below, latching the cap 480 and the shell 410 in effect completes the assembly of the cartomizer 200, and retains the various components shown in FIG. 4 in the correct position.

Above the end cap 480 is located the PCB 470, which includes a central air hole 471 to allow air to flow through the PCB 470 into the atomizer (the end cap 480 is likewise provided with a central air hole, not visible in FIG. 4, but apparent in FIG. 2) to support this airflow into the atomizer. In accordance with some embodiments, the PCB 470 does not contain any active electrical components, but rather provides a circuit or conductive path between the control unit 300 and the heater 450.

Above the PCB 470 is located the primary seal (cartomizer plug) 460, which has two main portions, an upper portion which defines (in part) an atomizer chamber (vapor generation chamber) 465, and a lower portion 462 which acts as an end seal for the reservoir 270. Note that in the assembled cartomizer 200, the reservoir 270 of e-liquid is located around the outside of the atomizer chamber, and the e-liquid is prevented from leaving the cartomizer 200 (at least in part) by the lower portion 462 of the cartomizer plug 460. The cartomizer plug 460 is made from a material that is slightly deformable. This allows the lower portion 462 to be compressed a little when inserted into the shell 410, and hence provide a good seal to retain the e-liquid in reservoir 270.

Two opposing side walls of the atomizer chamber 465 are provided with respective slots 569 into which the wick 440 is inserted. This configuration thereby helps to ensure the heater (vaporizer) 450, which is positioned on the wick 440, is located near the bottom of the atomizer chamber to vaporize liquid introduced into the atomizer chamber 465 by wick 440. In some embodiments, the wick 440 is made of glass fiber rope (i.e. filaments or strands of glass fiber twisted together), and the heater coil 450 is made of nichrome (an alloy of nickel and chromium) wire wound about the wick 440. However, various other types of wick and heater are known and could be used in the cartomizer 200, such as a wick made out of porous ceramic, and/or some form of planar heater (rather than a coil). Note that although FIG. 4 suggests that the heater coil 450 has a loop of wire dropping down from the wick 440 at each end, in practice there is just a single lead at each end.

The cartomizer plug 460 and the wick/heater assembly are surmounted by the inner frame 430, which has three main sections. The inner frame 430 is substantially rigid, and may be made of a material such as polybutylene terephthalate. The lowermost section 436 of the inner frame 430 covers the lower portion 462 of the cartomizer plug 460, while the middle section 434 completes the atomizer chamber 465 of the cartomizer plug 460. In particular, the inner frame 430 provides the top wall of the atomizer chamber 465, and also two side walls that overlap with the two side walls of the atomizing chamber 465 of the cartomizer plug. The final section of the inner frame 430 comprises an air channel wall/airflow tube 432 that defines an interior air channel that leads upwards from the top wall of the atomizing chamber 465 (part of the middle section 434) and couples with the mouthpiece hole 280. In other words, tube (air channel wall) 432 provides a passage (air channel) for vapor produced in the atomizing chamber (vapor generation chamber) 465 to be drawn along to exit the e-cigarette 100 for user inhalation through mouthpiece exit hole (vapor outlet) 280 in the mouthpiece end 250 of the vapor provision system/apparatus 100.

Since the inner frame 430 is substantially rigid, the vent seal 420 is provided at (inserted around) the top of the airflow tube 432 to help ensure a suitable seal between the inner frame 430 and the interior of the shell 410 around the mouthpiece exit hole 280. The vent seal 420 is made of a suitably deformable and resilient material such as silicone. Lastly, the shell 410 provides the external surface of the upper portion 220 of the cartomizer 200, including the mouthpiece 250, and also the lip or flange 240. The shell 410, like the end cap 480, is formed of a substantially rigid material, such as polypropylene. The lower section 412 of the shell 410 (i.e. below the lip 240) sits inside the end cap 480 when the cartomizer 200 has been assembled. The shell 410 is provided with a latch tab 413 on each side to engage with hole 261 on each side of the end cap 480, thereby retaining the cartomizer 200 in its assembled condition.

An airflow pathway through the cartomizer 200 enters a central hole 214 in the cap 480 (not visible in FIG. 4 but apparent in FIG. 2) and then passes through a hole 471 in the PCB 470. The airflow next passes up into the atomizer chamber 465, which is formed, at least in part, as part of the cartomizer plug 460, flows around the wick and heater assembly 500 and along the air channel defined by the tube (air channel wall) 432 of the inner frame 430 (and through vent seal 420), and finally exits through the hole 280 in the mouthpiece 250.

The reservoir 270 of e-liquid is contained in the space between this airflow pathway through the cartomizer 200 and the outer surface of the cartomizer 200. Thus shell 410 provides the outer walls (and top) of the housing for the reservoir 270, while the lower section 436 of the inner frame 430 in conjunction with the base portion 462 of the primary seal 460 and end cap 480 provide the bottom or floor of the housing for the reservoir 270 of e-liquid. The inner walls of this housing are provided by the atomizing (vapor generation) chamber 465 of the primary seal 460, in cooperation with the middle section 434 of the inner frame 430, and also the airflow tube 432 of the inner frame 430 and the vent seal 420. In other words, the e-liquid is stored in the reservoir space between the outer walls and the inner walls. Ideally, the e-liquid should not penetrate inside the inner walls, into the airflow passage, except via wick 440, otherwise there is a risk that liquid would leak out of the mouthpiece hole 280.

The capacity of this space is typically of the order of 2 ml in accordance with some embodiments, although it will be appreciated that this capacity will vary according to the particular features of any given design. Note that unlike for some e-cigarettes, the e-liquid reservoir 270 in this example is not provided with any absorbent material (such as cotton, sponge, foam, etc.) for holding the e-liquid. Rather, the reservoir chamber 465 only contains the liquid, so that the liquid can move freely around the reservoir 270. However, it will be appreciated this is not in itself significant to the principles described herein regarding the aspects of aerosol provision system relating to the air channel extending between the vaporizing chamber and the vapor outlet.

FIGS. 5A, 5B and 5C illustrate the wick/heater assembly being fitted into the cartomizer plug 460 in accordance with some embodiments of the disclosure. The wick/heater assembly 500 is formed from the heater wire 450 and the wick 440. As noted above, the wick 440 in this example comprises glass fibers formed into a generally cylindrical or rod shape. The heater/vaporizer 450 comprises a coil of wire 551 wound around the wick 440. At each end of the coil 551 there is a contact wire 552A, 552B, which together act as the positive and negative terminals to allow the coil 551 to receive electrical power.

As visible in FIG. 5A, the primary seal 460 includes the base portion 462 and the atomizing chamber 465. The base portion 462 is provided with two outwardly directed ribs. When the shell 410 is fitted over the base portion 462, these ribs are compressed slightly in order to fit inside the shell 410. This compression and the resulting slight resilient deformation of the ribs helps to ensure a good seal for the e-liquid at the base of the cartomizer reservoir 270.

Also visible in FIG. 5A, the vapor generation chamber 465 comprises four walls in a substantially rectangular arrangement, a pair of opposing side walls 568, and a pair of opposing front and back walls 567. Each of the opposing side walls 568 includes a slot 569 which has an open end at the top (and in the center) of the side wall 568, and a closed end 564 relatively near the bottom of the atomizing chamber 465—i.e. the two slots 569 extend more than halfway down their respective side walls 568.

Referring now to FIG. 5B, this shows the wick/heater assembly 500 now fitted into the atomizing chamber 465 of the cartomizer plug 460. In particular, the wick/heater assembly 500 is positioned so that it extends between, and protrudes out of, the two opposing slots 569A, 569B. The wick 440 is then lowered until it reaches the closed end 564 of each slot. Note that in this position, the coil 551 is located entirely in the atomizing chamber 465—it is only the wick itself 440 that extends out of the slots into the reservoir area 270. It will be appreciated that this arrangement allows the wick 440 to draw e-liquid from the reservoir 270 into the atomizing chamber 465 for vaporization by the wire heater coil 551. Having the wick 440 located near the bottom of the atomizing chamber 465, and more particularly also near the bottom of the reservoir 270, helps to ensure that the wick 440 retains access to liquid in the reservoir 270 even as the e-liquid is consumed, and hence the level of the e-liquid in the reservoir 270 drops. FIG. 5B also shows the heater contact wires 552A, 552B extending below the primary seal 460.

FIG. 5C illustrates the underside of the base portion 462 of the primary seal 460. This view shows that the base portion includes two holes 582A, 582B, which are used for filing the reservoir 270 with e-liquid, as described in more detail below. The underside further includes a rectangular indentation/recess 584 for receiving the PCB 470. A central hole 583 is provided in this indentation 584 to provide an air passage from underneath (and outside) the cartomizer 200 into the atomization (vaporization) chamber 465. It will be appreciated that after assembly, this central hole 583 in the cartomizer plug 460 is aligned with the corresponding central hole 471 in the PCB 470.

There are also two smaller holes 587A, 587B formed in the rectangular indentation 584 of the lower portion of the cartomizer plug 460, one on either side of the central hole 583. The contact wires 552A and 552B extend downwards from the heater 450 and pass respectively through these two holes, 587A, 587B, in order to exit the vaporizing chamber 465.

A slit 590A, 590B is formed in each of the front and back walls of the rectangular indentation 584. After extending through the two holes 587A, 587B, each contact wire 552A, 552B from the heater 450 is bent flat onto the underside of the cartomizer plug 460, and then leaves the rectangular indentation via the respective slits 590A, 590B. Thus contact wire 552A passes out of the atomizing chamber 465 through hole 587A, and then exits the rectangular indentation 584 via slot 590A; likewise, contact wire 552B passes out of the atomizing chamber 465 through hole 587B, and then exits the rectangular indentation 584 via slot 590B. The remaining portion of each wire 552A, 552B is then bent upwards towards the atomizing chamber 465 in order to sit within a respective groove 597 in the cartomizer plug 460 (see FIG. 5B).

Figure 6B:
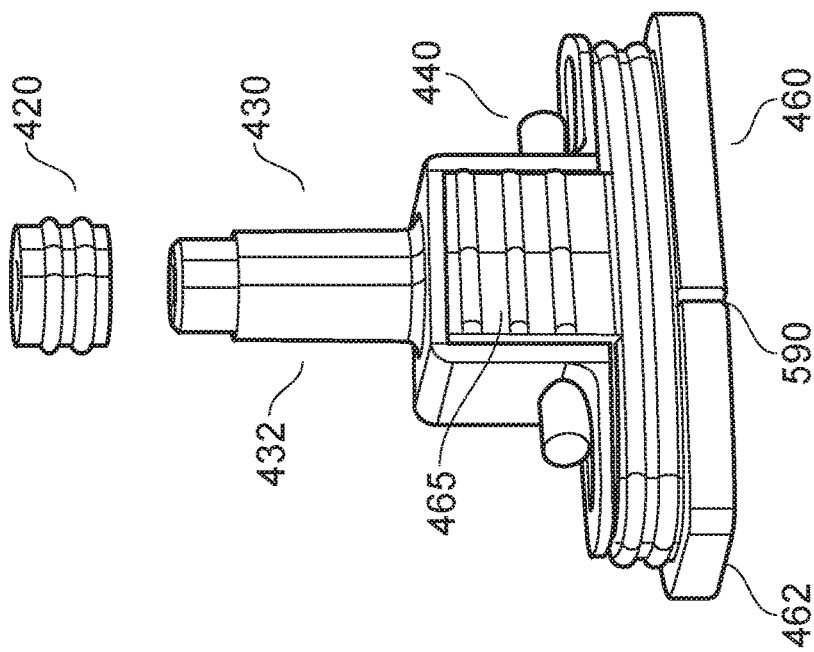
FIGS. 6A and 6B illustrate the inner frame and the vent seal being fitted into the cartomizer plug in accordance with some embodiments of the disclosure.
Figure 6A:
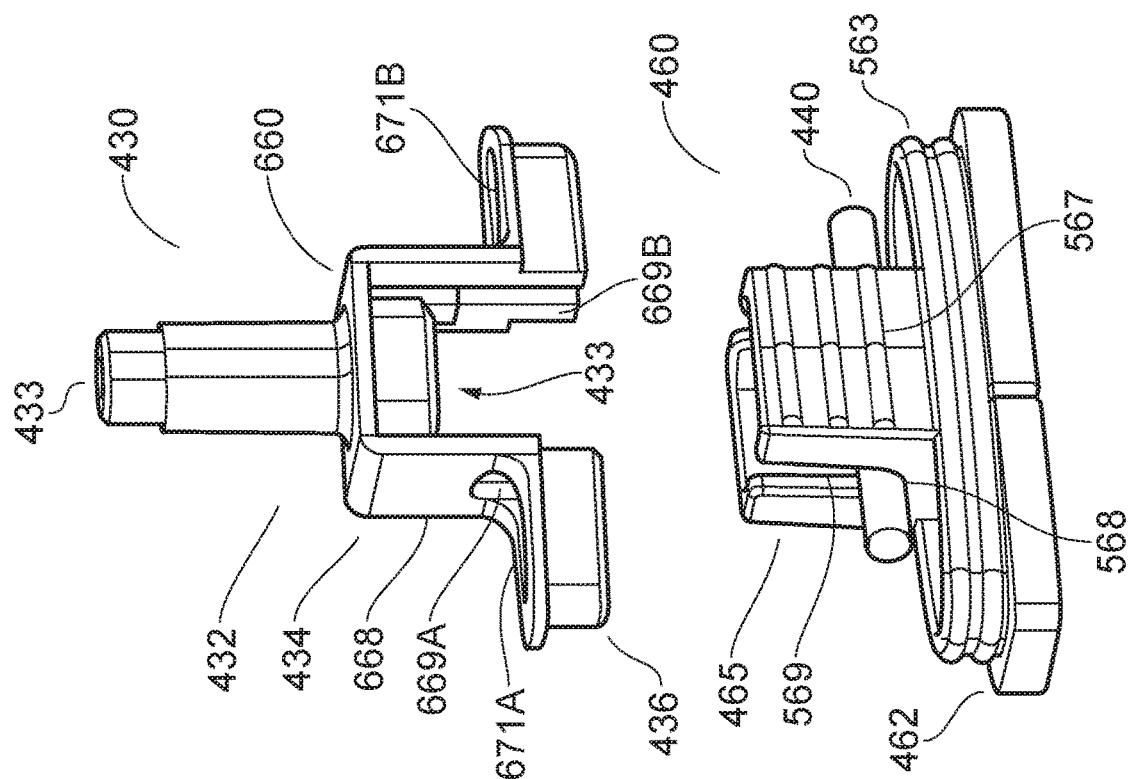

FIGS. 6A and 6B illustrate the inner frame 430 and the vent seal being fitted into the cartomizer plug 460 in accordance with some embodiments of the disclosure. Thus as previously described, the inner frame 430 comprises a base section 436, a middle section 434 and an upper section providing an air channel wall 432 defining an air channel providing fluid communication between the vapor generation chamber 465 and the vapor outlet 280 when the cartomizer 200 is assembled for use.

The base section 436 of the inner frame 430 contains two slots 671A, 671B extending in a horizontal sideways direction (parallel to the x-axis). As the base section 436 of the inner frame 430 is lowered down past the atomizing chamber 465, the portions of the wick 440 that extend out from each side of the atomizing chamber 465 pass through these slots 671A, 671B, thereby allowing the base section 436 of the inner frame 430 to be lowered further until it is received in the lower portion 462 of the cartomizer plug 460.

As noted above, the middle section 434 of the inner frame 430 complements and completes the vapor generation/atomizing chamber 465 of the cartomizer plug 460. In particular, the middle section 434 provides two opposing side walls 668 and a top wall or roof 660. The latter closes the top of the atomizing chamber 465, except in respect of the air tube 432 which extends up from the atomizing chamber 465 to the exit hole 280 of the mouthpiece 250.

Each of the opposing side walls 668 includes a slot 669A, 669B which extends upwards (parallel to the y-axis) from the bottom of the side wall 668 to the closed end of the respective slot 669A, 669B. Accordingly, as the base section 436 of the inner frame 430 is lowered down past the atomizing chamber 465, the portions of the wick 440 that extend out from each side of the atomizing chamber 465 pass through these slots 669A, 669B (in addition to slots 671A, 671B). This therefore allows the side walls 668 of the inner frame 430 to overlap the side walls 568 of the cartomizer plug 460. Further downward movement of the inner frame 430 is prevented once the closed end of slots 669A, 669B contacts the wick 440, which coincides with the base section 4436 of the inner frame 430 being received into the lower portion 462 of the cartomizer plug 460. At this stage, the combination of cartomizer plug 460, heater/wick assembly 500, and inner frame 430, as shown in FIG. 6B has been formed, and the vent seal 420 can now be fitted onto the air tube (pipe/air channel wall) 432 of the inner frame 430.

Figure 7B:
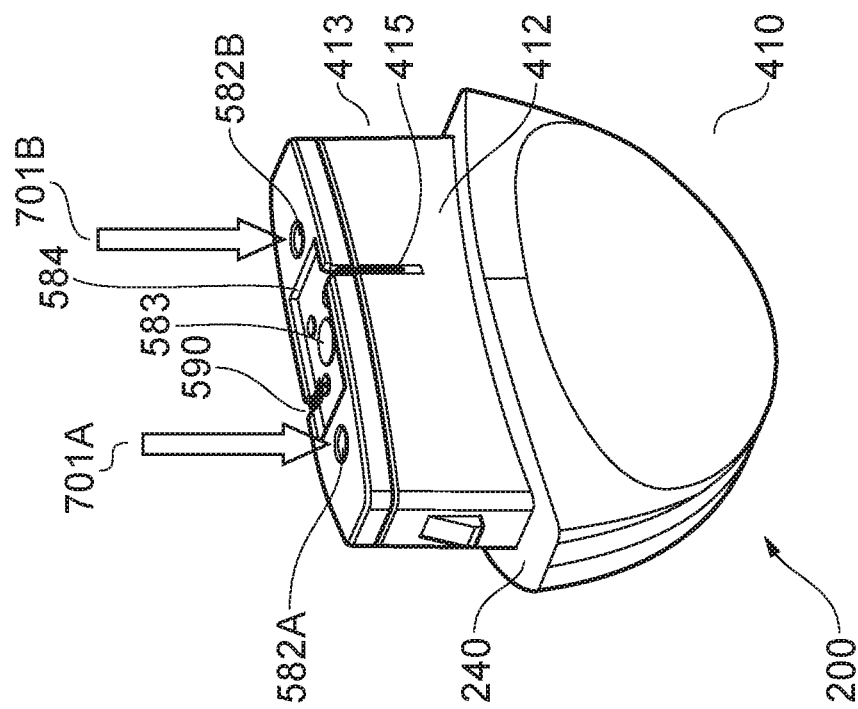
FIGS. 7A and 7B illustrate the combination of the inner frame, wick/heater assembly, and primary seal being fitted into the shell and the reservoir then being filled with e-liquid in accordance with some embodiments of the disclosure.
Figure 7A:
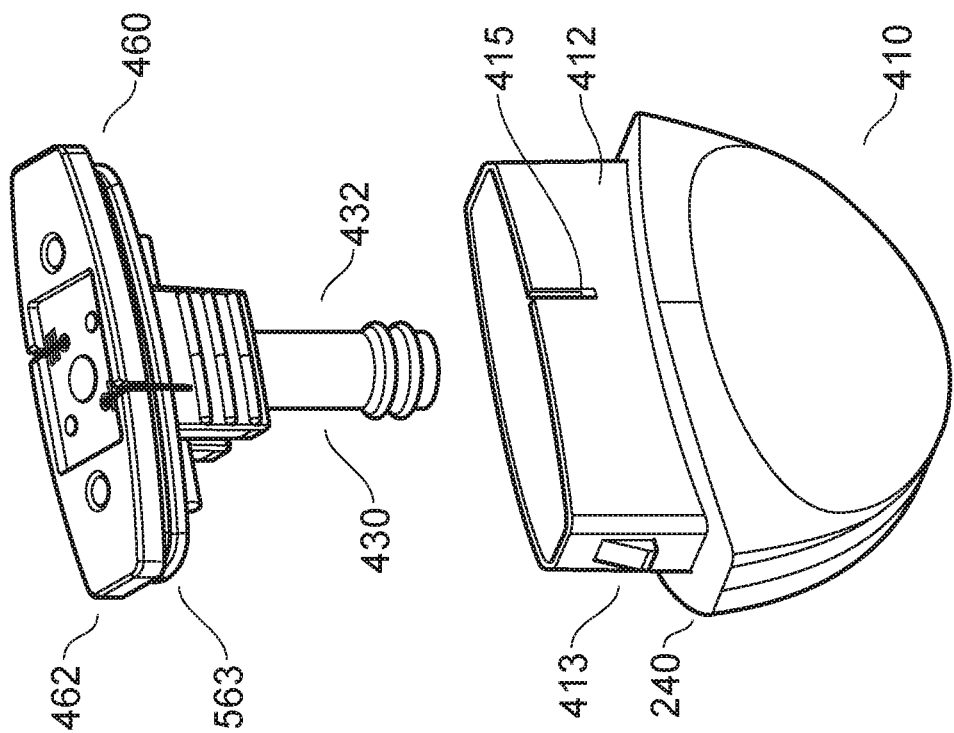

FIG. 7A illustrates the combination of the inner frame 430, wick/heater assembly 500, and primary seal 460 being fitted into the shell 410. As this insertion occurs, the slot 415 in each of the front and back faces of the lower portion 412 of the shell 410 accommodates a portion of wire 552 that has passed through slot 590 and has been wrapped back up around the outside of the cartomizer plug 460 and into groove 597. Furthermore, the deformable ribs 563 around the lower portion 462 of the primary seal 460 are slightly compressed by the inside wall of the lower portion 412 of the shell 410 during the insertion, and thereby form a seal to retain the e-liquid in the resulting reservoir 270. Accordingly, as illustrated in FIG. 7B, the cartomizer 200 is now ready for filling with the e-liquid. This filling is performed, as indicated by arrows 701A, 701B, through holes 582A and 582B in the primary seal 460, and through slots 671A, 671B in the inner frame (not visible in FIG. 7B).

Figure 8B:
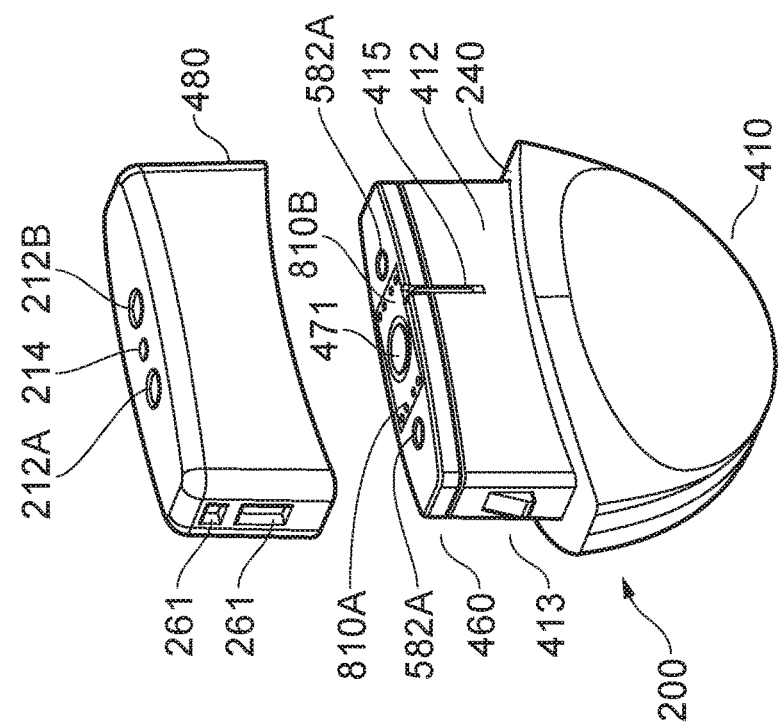
FIGS. 8A and 8B illustrate the PCB and end cap being fitted to the other components to complete the formation of the cartomizer in accordance with some embodiments of the disclosure.
Figure 8A:
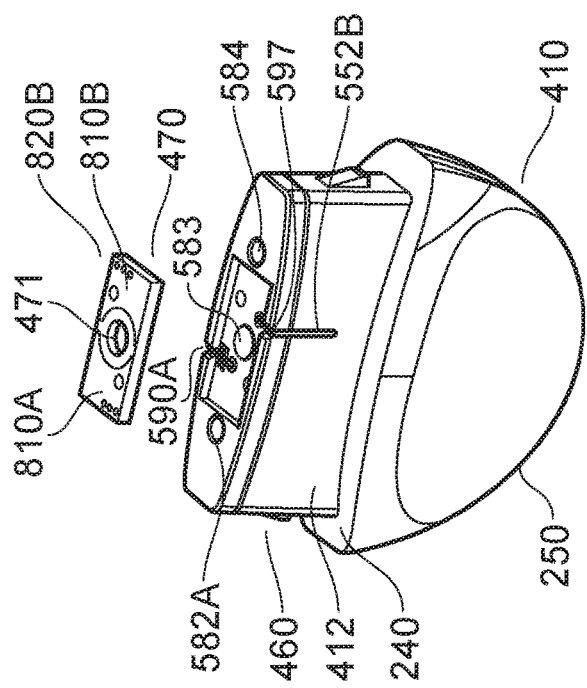

FIG. 8A illustrates the PCB 470 being fitted into the rectangular indentation 584 in the underside of the primary seal 460. This fitting aligns the central hole 471 in the PCB 470 with the central hole 583 in the primary seal 460 in order to provide the main airflow channel into the cartomizer 200.

As previously described, the rectangular indentation 584 is provided with a pair of holes 587, located on either side of the central hole 583. Each hole 587 allows egress of a respective contact wire 552A, 552B from the vaporizer chamber 465. The contact wires 552A, 552B are bent flat against the floor of the rectangular indentation 584, and then exit the rectangular indentation 584 via respective slots 590A, 590B in the front and back walls of the rectangular indentation 584. The final portion of each heater contact wire 552A, 552B, is then bent upwards, back towards the top of the cartomizer 200 and mouthpiece 250, and located in a corresponding groove or channel 597 formed in the cartomizer plug 460. In addition, the base portion of the shell 410 also includes a slot 415 on each of the front and back faces to accommodate a respective heater contact wire 552A, 552B.

In accordance with some embodiments, the PCB 470 does not contain any active components, but rather provides two large contact pads 810A, 810B on either side of the central hole 471. These contact pads are visible in FIG. 8A on the lower face of the PCB 470, i.e. the side facing the control unit 300 after assembly. The opposite face of the PCB 470, i.e. the upper side which is received into the rectangular indentation 584 and faces the heater 450, is provided with a similar, corresponding configuration of contact pads (not visible in FIG. 8A). The heater contact wires 552A, 552B are in physical, and hence electrical, contact with a respective contact pad on the upper side of the PCB 470.

The opposing pairs of contact pads 810A, 810B on either side of the PCB 470 are connected by respective sets of one or more vias 820A, 820B. In other words, vias 820A provide a conductive path between one contact pad on the lower face of the PCB 470 and a corresponding contact pad on the upper face of the PCB 470, and vias 820B provide a conductive path between the other contact pad on the lower face of the PCB 470 and its corresponding contact pad on the upper face of the PCB 470. Accordingly, when the control unit 300 is connected to the cartomizer 200, pins from the control unit 300 touch the contact pads on the lower side of the PCB 470, and electrical current flows to/from to/from the heater 450 through the respective vias, contact pads on the upper side of the PCB 470, and respective heater contact wires 552A, 552B.

FIG. 8B illustrates the end cap 480 being fitted to the cartomizer 200 in accordance with some embodiments of the disclosure. In particular, the end cap 480 is fitted over the end of the cartomizer plug 460 and the lower section 412 of the shell 410, and is retained in this position by the protruding member 413 provided on each side of the lower section 412 of the shell engaging into the corresponding hole or slot 261 on each side of the end cap 480. In this fully assembled state (see FIG. 2), the end cap 480 covers and therefore closes the holes 582A, 582B in the cartomizer plug 460 that were used for filling the liquid reservoir 270. Indeed, as can be seen in FIG. 10A, the end cap 480 is provided with two upwardly directed plugs 870A and 870B that respectively penetrate and close the filling holes 582A, 582B. Accordingly, the reservoir 270 is now fully sealed, apart from the opening on each side of the atomizing chamber 465 through which the wick 440 passes into the atomizing chamber 465.

As previously discussed, the end cap includes three holes, a central hole 214 and two holes 212A, 212B located on either side of this central hole. The fitting of the end cap 480 aligns the central hole 214 of the end cap with the central hole 471 in the PCB 470 and with the central hole 583 in the primary seal 460 in order to provide the main airflow channel into the cartomizer 200. The two side holes 212A, 212B allow pins from the control unit 300, acting as positive and negative terminals, to pass through the end cap 480 and make contact with respective contact pads 810A, 810B on the lower side of the PCB 470, thereby enabling the battery 350 in the control unit 300 to supply power to the heater 450.

In accordance with some embodiments, the primary seal 460, which as noted above is made of a resilient deformable material such as silicone, is held in a compressed state between the inner frame 430 and the end cap 480. In other words, the end cap 480 is pushed onto the cartomizer 200 and compresses the primary seal 460 slightly before the latch components 413 and 261 engage with one another. Consequently, the primary seal 460 remains in this slightly compressed state after the end cap 480 and shell 410 are latched together. One advantage of this compression is that the end cap 480 acts to push the PCB 470 onto the heater contact wires 552A, 550B, thereby helping to ensure a good electrical connection without the use of solder.

Figure 9:
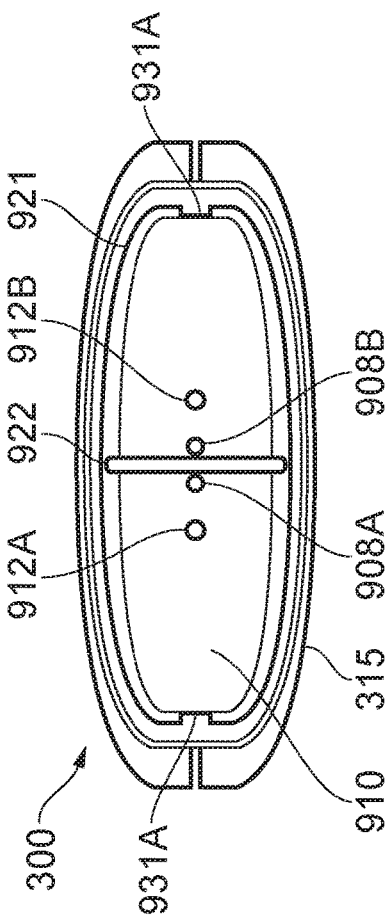
FIG. 9 is a top view looking down onto the control unit of the e-cigarette of FIG. 1 in accordance with some embodiments of the disclosure.

FIG. 9 is a top view looking down onto the control unit 300 of the e-cigarette 100 of FIG. 1 in accordance with some embodiments of the disclosure. The control unit 300 includes external walls 315 that rise above the rest of the control unit 300 (as best seen in FIG. 1) to define a cavity for accommodating the lower portion 210 of the cartomizer 200. Each side of these walls 315 is provided with a spring clip 931A, 931B that engages with the hole or slot 260 on each side of the cartomizer 200 (see FIG. 2), thereby retaining the cartomizer 200 in engagement with the control unit 300 to form the assembled e-cigarette 100.

At the bottom of the cavity formed by the upper portion of control unit walls 315 (but otherwise at the top of the main body of the control unit 300) is a battery seal 910 (see also FIG. 1). The battery seal 910 is formed from a resilient (and compressible) material such as silicone. The battery seal 910 helps to mitigate one potential risk with an e-cigarette 100, which is that e-liquid leaks from the reservoir 270 into the main air passage through the device 100 (this risk is greater where there is free liquid in the reservoir 270, rather than the liquid being held by a foam or other such material). In particular, if e-liquid were able to leak into the portion of the control unit 300 containing the battery 350 and control electronics, then this might short circuit or corrode such components. Furthermore, there is also a risk that the e-liquid itself would then become contaminated before returning into the cartomizer 200 and then exiting through the mouthpiece hole 280. Accordingly, if any e-liquid does leak into the central air passage of the cartomizer 200, the battery seal 910 helps to prevent such leakage progressing into the portion of the control unit 300 that contains the battery 350 and control electronics. (The small holes 908 in the battery seal 910 do provide very limited fluid communication with the microphone 345 or other sensor device, but the microphone 345 itself can then act as a barrier against any such leakage progressing further into the control unit 300.)

As shown in FIG. 9, there is a small groove or spacing 921 around the perimeter between the top of the battery seal 910 and the inside of the walls 315 of the control unit 300; this is primarily formed by the rounded corner of the battery seal 910. The battery seal 910 is further provided with a central groove 922 from front to back, which connects at both ends (front and back) with the perimeter groove 921 to support airflow into the cartomizer 200, as described in more detail below. Immediately adjacent to central groove 922 are two holes 908A, 908B, one on either side of the groove 922. These air holes extend down to the microphone 345. Thus when a user inhales, this causes a drop in pressure within the central air passage through the cartomizer 200, as defined by air tube 432, the central hole 583 in the primary seal 460, etc., and also within the central groove 922, which lies at the end of this central air passage. The drop in pressure further extends through holes 908A, 908B to the microphone 345, which detects the drop in pressure, and this detection is then used to trigger activation of the heater 450.

Also shown in FIG. 9 are two contact pins, 912A, 912B, which are linked to the positive and negative terminals of the battery 350. These contact pins 912A, 912B pass through respective holes in the battery seal 910 and extend through holes 212A, 212B of the end cap to make contact with contact pads 810A, 810B respectively on the PCB 470. Accordingly, this then provides an electrical circuit for supplying electrical power to the heater 450. The contact pins 912A, 912B may be resiliently mounted within the battery seal 910 (sometimes referred to as "pogo pins"), such that the mounting is under compression when the cartomizer 200 is latched to the control unit 300. This compression causes the mounting to press the contact pins 912A, 912B against the PCB contact pads 810A, 810B, thereby helping to ensure good electrical connectivity.

The battery seal 910, which as noted above is made of a resilient deformable material such as silicone, is held in a compressed state between the cartomizer 200 and the control unit 300. In other words, inserting the cartomizer 200 into the cavity formed by walls 315 causes the end cap 480 of the cartomizer 200 to compress the battery seal 910 slightly before the spring clips 931A, 931B of the control unit 300 engage with the corresponding holes 260A, 260B in the lower portion 210 of the cartomizer 200. Consequently, the battery seal 910 remains in this slightly compressed state after the cartomizer 200 and the control unit 300 are latched together, which helps to provide protection against any leakage of e-liquid, as discussed above.

FIGS. 10A and 10B are cross-sections respectively (a) from side to side, and (b) from front to back, showing the airflow through the e-cigarette of FIG. 1 in accordance with some embodiments of the disclosure. The airflow is denoted in FIGS. 10A and 10B by the heavy black, dashed arrows. (Note that FIG. 10A only shows airflow on one side of the device, but there is an analogous airflow on the other side as well—having multiple such air inlets reduces the risk that a user will accidentally block the air inlets with their fingers while holding the device 100.)

The airflow enters through a gap at the sides of the e-cigarette 100, in between the top of the walls 315 of the control unit 300, and the flange or rim 240 of the cartomizer shell 410. The airflow then passes down a slight spacing between the inside of the walls 315 and the outside of the lower portion 210 of the cartomizer 200, past the spring clips 931, and hence into perimeter groove 921 (as shown in FIG. 9). The airflow is then drawn around the perimeter groove 921, and hence out of the plane of FIGS. 10A and 10B (so that this portion of the airflow path is therefore not visible in these two diagrams). Note that there is typically some space above the groove 921 between the inside of the control unit 300 walls and the outside of the cartomizer end cap 480, so the airflow is not necessarily constrained to the groove 921 per se.

After travelling an angle of approximately 90 degrees around the perimeter groove 921, the airflow passes into the central groove 922, from where it travels to and through the central hole 583 of the end cap 480 and hence into the central air passage of the cartomizer 200 upstream of the vapor generation chamber 465 (i.e. further from the vapor outlet 280 than the vapor generation chamber 465). Note that FIG. 10B shows this airflow along the central groove 922 into the central air passage, and then the flow of air up through the central air passage is shown in both FIGS. 10A and 10B. In contrast to groove 921, the space above groove 922 is not open, but rather the battery seal 910 is compressed against the end cap 480 of the cartomizer 200. This configuration results in the end cap 480 covering the groove 922 to form a closed channel having a confined space. This confined channel can be utilized to help control the draw resistance of the e-cigarette 100.

After entering the cartomizer 200 through the air inlet holes 214, the airflow passes into the vapor generation chamber 465 where it mixes with vapor generated by the vaporizer. The vapor is then carried by the air along the air channel 33 defined by the air channel wall 432 (provided by the inner frame component of the cartomizer 200 as discussed above).

Thus, the cartomizer 200 comprises a vapor provision apparatus which, when coupled to the control unit 300, forms a vapor provision system in which the cartomizer 200 comprises a vapor generation chamber 465 containing a vaporizer (e.g. electric heater) 450 for generating vapor from a vapor precursor material/e-liquid. The cartomizer 200 further comprises an air channel wall 432 defining an air channel 433 between the vapor generation chamber 465 and a vapor outlet 280 through which vapor exits the device 100 when in use. In accordance with certain embodiments of the disclosure, and as discussed further below, an inner surface of the air channel wall is provided with at least one protrusion which extends into the air channel to modify/redirect/disrupt a flow of air in the air channel 433 during use. This approach can help to improve the nature of the aerosol delivered received by users. For example, and without being bound by theory, approaches in accordance with the principles described herein may be considered to enhance an intermixing of the air drawn into the cartomizer 200 from the environment through the air inlet 214 and the vapor generated in the vapor generation chamber 465 by the vaporizer 450 to provide a more uniform/consistent vapor.

Figure 11A:
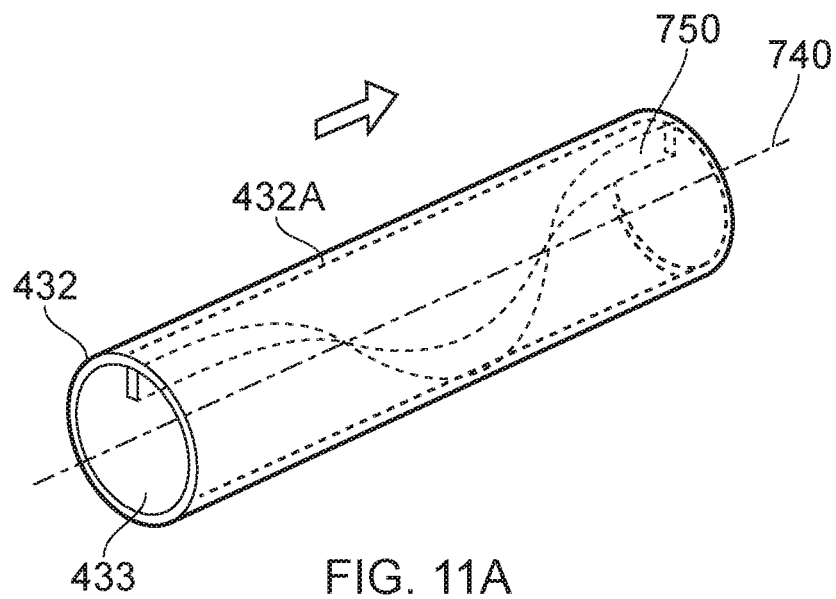
Figures 11B, 11C:
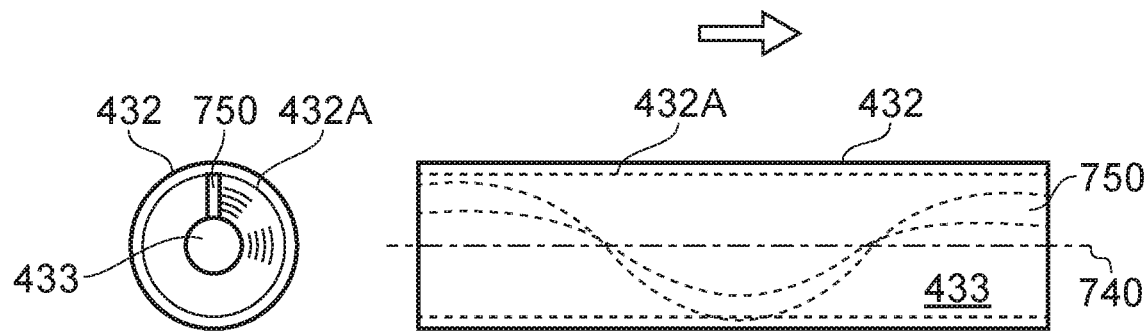

FIGS. 11A to 11C are highly schematic views of the air channel wall 432 defining the air channel 433 extending along an axis of extent 740 in accordance with certain embodiments of the disclosure. FIG. 11A schematically represents a perspective view of the air channel wall 432 with elements hidden behind the outer surface of the air channel wall 432 shown in dashed line. FIG. 11B schematically represents an end view of the air channel wall 432, in this example the left-hand end of the representation of FIG. 11A (i.e. a view parallel to the y-axis represented in FIG. 1). FIG. 11C schematically represents a side view of the air channel wall 432 (i.e. a view parallel to the x-axis represented in FIG. 1). The direction of normal airflow when the cartomizer 200 is in use is indicated in FIGS. 11A and 11C by an arrow. For ease of representation, the air channel wall 432 represented in FIGS. 11A to 11C is shown as comprising a generally cylindrical shape with structural features associated with the coupling of the air channel 433 to the vapor generation chamber 465 and the vapor outlet 280 (via the outlet seal 420) not being shown for simplicity.

Also represented in FIGS. 11A to 11C is an inner wall 432A of the air channel wall 432 which defines an outer surface of the air channel 433 through which airflows when the vapor provision system 100 is use. As also schematically represented in these figures, the air channel wall 432 includes a protrusion 750 extending into the air channel 433 from a part of the inner wall 432A. In this example the protrusion is in the form of a protrusion wall running the length of the portion of the air channel 433 represented in FIG. 11 along a generally helical path, completing around one turn.

The helical/spiral path of the protrusion 750 along the length of the air channel 433 means the protrusion provides a wall that extends into the air channel 433 with a surface facing air drawn along the channel 433 and inclined at a non-zero angle to the axis of extent 740 of the air channel 433 (i.e. an axis corresponding generally to the direction of airflow in use). This causes air passing along the channel 433 to be deflected about the central axis of the airflow tube (in this example in a clockwise direction as viewed from the upstream end), thereby imparting a degree of rotation about the axis of extent of the air channel 433 to the air flowing through the air channel 433. Thus, the protrusion 750 causes the flow of air in the air channel 433 to be modified during use, in this case by introducing rotation.

The degree of rotation will depend on various factors, such as the size of the protrusion 750 (i.e. how far it extends into the airflow channel 433 (its height), the inclination of the deflecting wall provided by the protrusion to the axis of extent 740, and the number of protrusions 750). In the example represented in FIGS. 11A to 11C, the airflow channel 433 has a diameter of around 5 mm and the protrusion extends into the airflow channel 433 for a distance of around 2 mm. The protrusion 750 presents a relatively shallow angle to incoming air, for example around 15 degrees. Furthermore, in this example there is only one protrusion 750.

If a greater degree of airflow modification (i.e. more rotation) is desired, a greater number of walls, for example one or more further protrusion walls 750, could be added with an appropriate azimuthal offset from the protrusion wall 750 represented in FIGS. 11A to 11C (e.g. 180 degrees offset for one further wall, 120 degrees offset for each of two further walls, etc.). Also, the extent of the protruding wall(s) 750 (or other protrusions/ridges) into the air channel 433 could be increased to increase the modification to the airflow. Furthermore still, a tighter spiral (i.e. more turns along the length of the air channel 433) could be used to provide an increase in the deflection angle presented to air flowing in the air channel 433. For example, in some examples the deflection angle may be selected from the group comprising: at least 10 degrees; at least 20 degrees; at least 30 degrees; at least 40 degrees; at least 50 degrees; at least 60 degrees; at least 70 degrees; and at least 80 degrees.

To introduce a smaller degree of rotation, the protruding wall 750 could be made smaller, or it may be broken into a number of non-continuous portions along the helical path. More generally, it will be appreciated there are many parameters for the configuration of one or more protrusions 750 which could be adjusted to provide a desired degree of rotation. An appropriate degree of rotation for any given implementation could be determined empirically, for example, by testing the performance of different example configurations.

In some respects the approaches of introduction of rotation into airflow along the air channel 433 may be considered to providing a rifling effect.

Figures 12A, 12B:
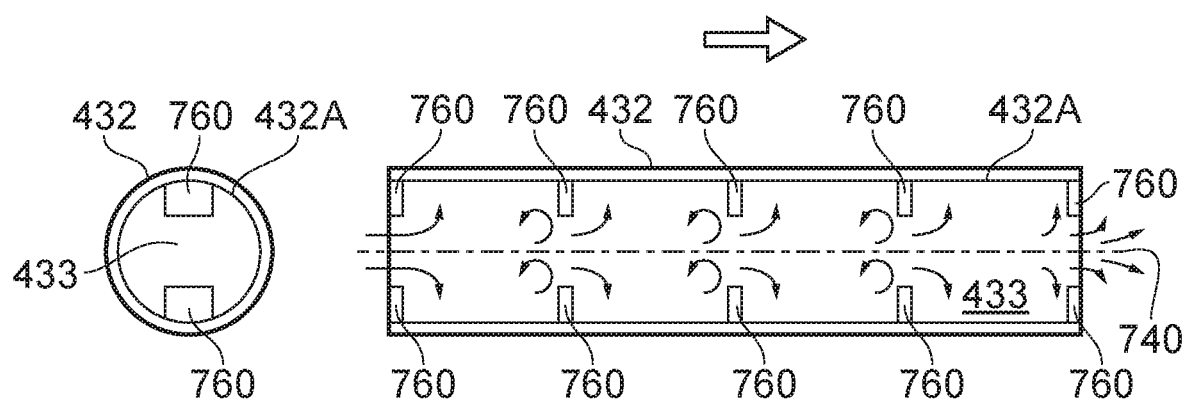

FIGS. 12A and 12B are similar to, and will be understood from, FIGS. 11B and 11C, but show a different protrusion configuration. In particular, rather than a single ribbon-like helical protrusion 750 from an inner wall 432A of the air channel wall 432, in the example of FIGS. 12A and 12B, there are a plurality of separate protrusions 760 extended inwardly from the inner wall 432A defining the air channel 433. These protrusions 760 provide surfaces facing the direction of airflow more or less square on (i.e. the major surfaces of the respective protrusions 760 facing the oncoming air are substantially orthogonal to the axis of extent 740 of the airflow channel 433/direction of airflow). Accordingly, rather than introduce rotation into the airflow, this configuration introduces turbulence, as schematically indicated by the airflow arrows shown within the air channel 433. It will again be appreciated the specific arrangement of protrusions will depend on the degree of airflow modification required. For example, in FIGS. 12A and 12B the individual protrusions 760 extend around a relatively small azimuthal extent, whereas in other examples they may extend around a greater azimuthal extent, perhaps forming closed rings, to provide an increased degree of airflow modification/turbulence in the air channel 433. Similarly, a higher or lower number of protrusions 760 may be provided along the axial extent of the airflow path 433 to increase or decrease the degree of airflow modification in the air channel 433 due to the protrusions 760.

In terms of their structure, the protrusions 750, 760 and the airflow wall 732 represented in the respective embodiments of FIGS. 11A to 11C and FIGS. 12A to 12B may in each case be integrally formed, e.g. with appropriate molding and/or machining techniques. However, in other examples in which an inner surface of the air channel wall 732 is provided with at least one protrusion 750, 760 extending into the air channel 433 in accordance with the principles described herein, the at least one protrusion 750, 760 may be formed separately from the air channel wall 732 and instead comprise a separate insert for the air channel 433.

FIGS. 13A, 13B and 13C are generally similar to, and will be understood from, FIGS. 11A, 11B and 11C. However, whereas in the example of FIGS. 11A, 11B and 11C, the airflow modification (rotation) is achieved using a protrusion comprising a helical wall integrally formed with the air channel wall 432, in the example of FIGS. 13A, 13B and 13C, a protrusion 770 comprising a helical spring-shaped structure is inserted into the air channel 433 which is defined by an otherwise smooth inner wall 432A. In this example the helical spring-shaped structure 770 comprises a conventional spring having an appropriate outer diameter and thickness (gauge). In this regard, the thickness of the spring 770 providing the protrusion in FIGS. 13A to 13B is in this example less than the height of the wall 750 providing the protrusion in FIGS. 11A to 11B, but the spring 770 is arranged to present a steeper angle to incoming air (i.e. arranged on a tighter helix with more turns) and so may introduce a broadly corresponding degree of rotation to air flowing in the air channel 433. In any event, and as discussed above, an appropriate configuration providing a desired degree of airflow modification can be established through empirical testing, for example by assessing the performance using springs of different dimensions.

Figure 14A:
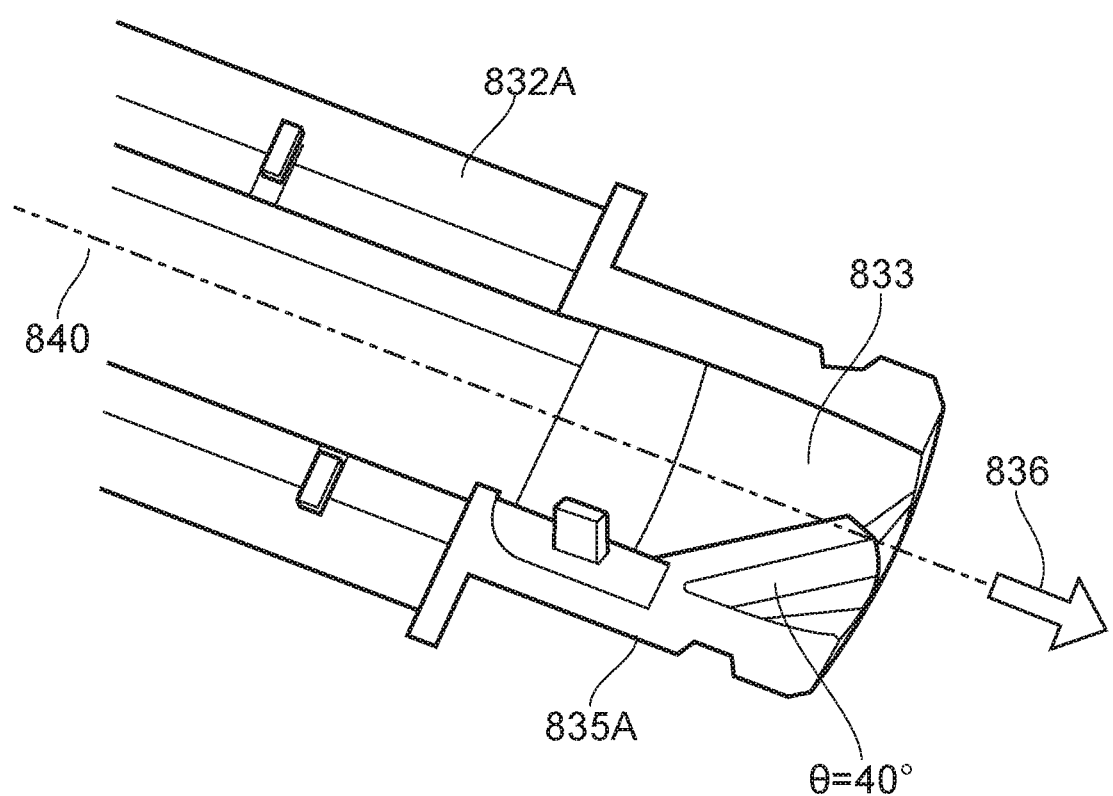
Figure 14B:
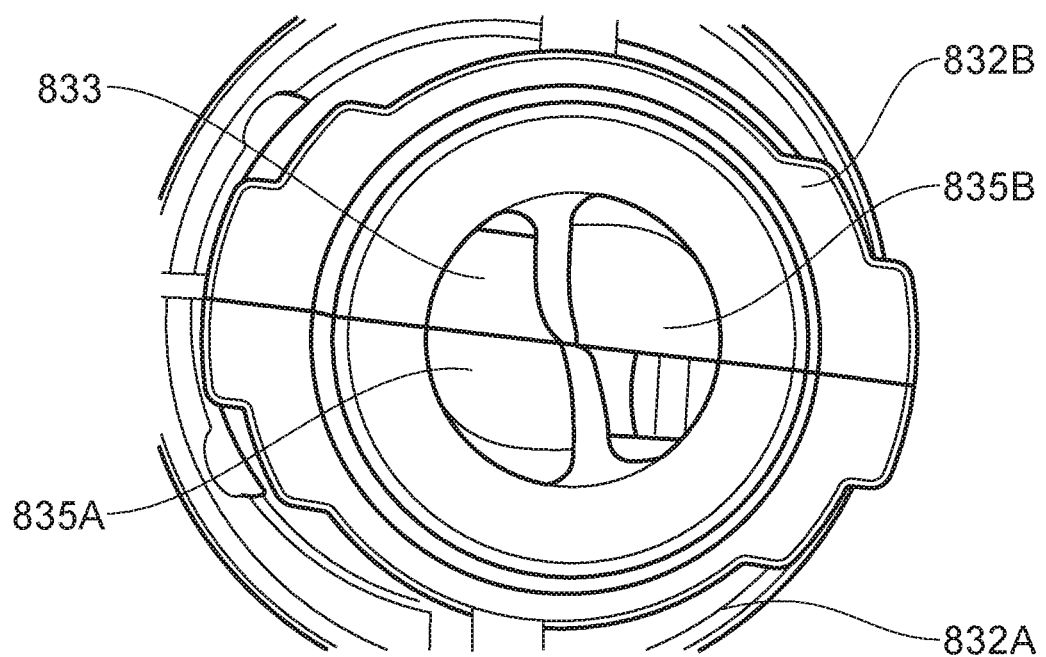

FIGS. 14A and 14B schematically represent portions of an air channel wall 832 defining an air channel 833 extending along an axis of extent 840 and which includes protrusions 835A and 835B for use in a cartomizer 200 in accordance with certain embodiments of the disclosure. The direction of normal airflow when the cartomizer 200 is in use is indicated in FIG. 14A by an arrow 836. In this example the air channel wall 832 is manufactured as two parts with each part being integrally molded, e.g. from a plastic material, with a respective one of the protrusions 835A, 835B. Thus the air channel wall 832 comprises a first part 832A and a second part 832B which are assembled to define a generally tubular air channel 833 with the protrusions 835A, 835B extending into the air channel 833 to modify airflow in accordance with the principles described herein. In both FIGS. 14A and 14B only a portion of the air channel wall 832 in the vicinity of the protrusions 835A, 835B is shown for simplicity, and furthermore, only the first half of the air channel wall 832A is shown in FIG. 14A.

It will be appreciated these kinds of protrusions can be incorporated in an air channel regardless of the overall construction and operation of the remaining parts of the electronic cigarette and in that sense, the manner in which the air channel wall 832 is incorporated into an electronic cigarette, for example in terms of sealing and coupling to other parts of the electronic cigarette, is not significant to the principles described herein.

In terms of scale, the air channel wall 832 in this specific implementation example has an outer diameter of around 6 mm and an inner diameter of around 3 mm (i.e. wall thickness is around 1.5 mm) in the vicinity of the protrusions. The respective protrusions 835A, 835B have a length of around 4 mm and are inclined in this example is an angle of around 40° to the air channel wall. The protrusions 835A, 835B have a thickness of around 0.5 mm and a height of around 1.5 mm. Consequently, when the two halves of the air channel wall 832 are assembled together for use, the respective protrusions 835A, 835B are close to meeting at the centre of the air channel 833, as can be seen in FIG. 14B.

In that sense the protrusions 835A, 835B are arranged to extend from the air channel wall to around the center of the air channel 833 so that together they span the majority, e.g. more than 50%, 60%, 70%, 80% or 90% of the air channel diameter, and in some cases the individual protrusions 835A, 835B may extend from the wall 832 to be on the center of the air channel 833 so that protrusions 835A, 835B on one side of the air channel 833 overlap with protrusions 835A, 835B on the other side of the air channel 833. That is to say a protrusion 835A, 835B may extend from the air channel wall 832 towards a central axis of the air channel 833 for a distance corresponding to at least 50%, 60%, 70%, 80%, 90% and 100% of the distance between the air channel wall 832 and the central axis.

For arrangement discussed above in which the protrusions comprise two angled walls (vanes) extending from the air channel wall 832 to around the center of the air channel 833 at around the same location along the axis of the air channel 833, it will be appreciated when viewed along the axis of the air channel 833, the protrusions cover around 50% of the cross-sectional area of the air channel 833. However, it will be appreciated that in other examples the protrusions may cover different amounts of the cross sectional area of the air channel, for example having regard to a desired increase in draw resistance provided by the protrusions. For example, in other cases the protrusions may cover, in projection, between 20% and 80%, between 30% and 70%, or between 40% and 60% of the cross-sectional area of the airflow channel in a plane perpendicular to its axis of extent.

It will be appreciated the specific example sizes and shapes set out above are merely for one particular implementation and other implementations may have different geometries, for example different sizes having regard to the overall structure of the cartomizer 200 in which the air channel is provided. Furthermore it will be appreciated the specific example of an angle of inclination for the respective protrusions of 40 degrees to the air channel wall/longitudinal axis of the air channel is again merely one particular implementation. Other angles may be used in other implementations, for example angles in the range 10 degrees to 70 degrees, 20 degrees to 60 degrees and 30 degrees to 50 degrees.

Approaches in accordance with the examples discussed above in relation to FIGS. 14A and 14B, i.e. consisting of two protrusions arranged to almost meet at the centre of the air channel, have been found to provide an appropriate degree of modification to airflow without generating an undesirably high increase in draw resistance and/or condensation in use.

Thus, in accordance with the principles described herein, an air channel providing fluid communication between a vapor generation chamber and a vapor outlet opening in an aerosol provision apparatus, for example a cartomizer for coupling to a control unit comprising a battery for selectively supplying power to the vaporizer in the vapor generation chamber, is provided with a means (e.g. one or more protrusions) for modifying the flow of air in the air channel, for example by imparting a degree of rotation and/or a degree of turbulence. As noted above, this can help provide a vapor/aerosol with improved characteristics in terms of user perception.

Thus, there has been described a vapor provision apparatus (e.g. a detachable cartridge for a vapor provision system) comprising: a vapor generation chamber containing a vaporizer for generating vapor from a vapor precursor material; and an air channel wall defining an air channel between the vapor generation chamber and a vapor outlet at a mouthpiece end of the vapor provision apparatus through which a user can inhale vapor during use; wherein an inner surface of the air channel wall is provided with at least one protrusion extending into the air channel to modify (redirect) a flow of air in the air channel during use. For example, the at least one protrusion may be arranged to define one or more portions of a helical wall extending into the air channel so as to impart a degree of rotation about an axis of extent of the air channel to air flowing in the air channel during use.

While some particular examples have been described above, it will be appreciated there are many modifications that could be made in accordance with other implementations.

For example, it will be appreciated some embodiments may incorporate features of different embodiments discussed above, for example a combination of turbulence inducing protrusions and rotation inducing protrusions.

It will also be appreciated the specific shape and configuration of the various elements discussed above may be modified for different implementations, for example in accordance with a desired overall size and shape of the electronic cigarette. For example, the system need not be generally flat, but could be more cylindrical, while still making use of the principles described herein in respect of airflow along an air channel connecting a vaporization chamber to a vapor outlet.

It will further be appreciated that whereas the above-described embodiments have primarily focused on an electrical heater based vaporizer, the same principles may be adopted in accordance with vaporizers based on other technologies, for example piezoelectric vibrator based vaporizers.

It will similarly be appreciated that whereas the above-described embodiments have primarily focused on liquid-based aerosol provision systems, the same principles for manipulating the flow of air in an outlet air channel of a vapor provision system can equally be applied in respect of systems for generating vapor from a solid, or other non-liquid, precursor material, for example an aerosol provision system based on heating tobacco or a tobacco derivative could also make use of the principles described herein.

Although various embodiments have been described in detail herein, this is by way of example only, and as already noted, it will be appreciated that approaches in accordance with the principles described herein may be utilized in many different configurations. For example, these approaches might be used for a one-piece or three-piece device (rather than a two-piece device, i.e. cartomizer and control unit, as described here). Similarly, as already noted, these approaches could be utilized with electronic vapor provision systems that includes non-liquid aerosol precursor material, for example material derived from tobacco plants which is provided in another (e.g. powder, paste, shredded leaf material, etc.), and then heated to produce volatiles for inhalation by a user. The approaches described herein could also be used with various types of heater for the e-cigarette, various types of airflow configuration, various types of connection between the cartomizer and the control unit (such as screw or bayonet) etc. The skilled person will be aware of various other forms of electronic vapor provision system which might employ approaches of the kind discussed above.

More generally, it will be appreciated the various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in future.

The invention claimed is:

1. A vapor provision apparatus comprising:
 a vapor generation chamber containing a vaporizer for generating vapor from a vapor precursor material; and
 an air channel wall defining an air channel between the vapor generation chamber and a vapor outlet at a mouthpiece end of the vapor provision apparatus through which a user can inhale vapor during use;
 wherein an inner surface of the air channel wall is provided with at least one protrusion extending into the air channel to modify a flow of air in the air channel by imparting a degree of rotation about an axis of extent of the air channel during use;
 wherein the at least one protrusion defines at least one protrusion wall extending into the air channel and having a surface inclined at a non-zero angle of at least 10 degrees to the axis of extent of the air channel; and
 wherein the at least one protrusion covers between 20% and 80% of a cross-sectional area of the airflow channel in a plane perpendicular to the axis of extent of the air channel.

2. Vapor provision means comprising:
 vapor generation chamber means containing vapor generation means for generating a vapor from vapor precursor material means; and
 air channel wall means defining air channel means fluidly connecting between the vapor generation chamber means and vapor outlet means at a mouthpiece end of the vapor provision means through which a user can inhale vapor during use;
 wherein an inner surface of the air channel wall means is provided with protrusion means extending into the air channel means for modifying a flow of air in the air channel means by imparting a degree of rotation about an axis of extent of the air channel means during use; and
 wherein the at least one protrusion means defines at least one protrusion wall means extending into the air channel means and having a surface inclined at an angle of at least 10 degrees to the axis of extent of the air channel means; and
 wherein the at least one protrusion means covers between 20% and 80% of a cross-sectional area of the airflow channel means in a plane perpendicular to the axis of extent of the air channel means.

3. The vapor provision apparatus of claim 1, wherein the non-zero angle comprises an angle selected from the group consisting of: at least 20 degrees; at least 30 degrees; at least 40 degrees; at least 50 degrees; at least 60 degrees; at least 70 degrees; and at least 80 degrees.

4. The vapor provision apparatus of claim 1, wherein the at least one protrusion wall is arranged on a helical path extending along at least a part of the air channel wall so as to impart a degree of rotation about the axis of extent of the air channel to air flowing along the air channel during use.

5. The vapor provision apparatus of claim 1, wherein the at least one protrusion is arranged to introduce a degree of turbulence to air flowing along the air channel during use.

6. The vapor provision apparatus of claim 1, wherein the at least one protrusion and the air channel wall are integrally formed.

7. The vapor provision apparatus of claim 1, wherein the at least one protrusion is formed separately from the air channel wall and comprises an insert for the air channel.

8. The vapor provision apparatus of claim 7, wherein the insert comprises a helical spring.

9. The vapor provision apparatus of claim 1, wherein the vapor provision apparatus is a detachable cartridge for a vapor provision system comprising the detachable cartridge and a control unit, wherein the control unit comprises a power supply for selectively supplying power to the vaporizer when the detachable cartridge is coupled to the control unit for use.

10. The vapor provision apparatus of claim 1, further comprising a power supply for selectively supplying power to the vaporizer.

11. The vapor provision apparatus of claim 1, wherein the vaporizer comprises a heater in proximity to at least a portion of the vapor precursor material.

12. The vapor provision apparatus of claim 1, wherein the vapor precursor material comprises a liquid.

13. The vapor provision apparatus of claim 1, wherein the vapor precursor material comprises a solid material.

14. The vapor provision apparatus of claim 1, wherein the at least one protrusion defines the at least one protrusion wall extending into the air channel and having a surface inclined at the non-zero angle to the axis of extent of the air channel, wherein the non-zero angle comprises an angle within a range of one of: 10 degrees to 70 degrees; 20 degrees to 60 degrees; or 30 degrees to 50 degrees.

15. The vapor provision apparatus of claim 1, wherein the at least one protrusion extends from the air channel wall towards a central axis of the air channel by a distance of at least one of: 50%, 60%, 70%, 80%, 90% or 100% of a distance between the air channel wall and the central axis.

16. The vapor provision apparatus of claim 1, wherein the at least one protrusion comprises two protrusions, and the air channel wall is formed of a first wall part and a second wall part, and wherein each of the first wall part and the second wall part is integrally molded with one of the two protrusions.

17. The vapor provision apparatus of claim 1, wherein the at least one protrusion comprises two protrusions which extend into the air channel at the same location along the axis of extent of the air channel.

18. The vapor provision apparatus of claim 1, wherein the at least one protrusion covers one of between 30% and 70% or between 40% and 60% of the cross-sectional area of the airflow channel in a plane perpendicular to the axis of extent of the airflow channel.

* * * * *

UNITED STATES PATENT AND TRADEMARK OFFICE
CERTIFICATE OF CORRECTION

PATENT NO. : 11,241,043 B2  
APPLICATION NO. : 16/087019  
DATED : February 8, 2022  
INVENTOR(S) : David Leadley and Jeremy Wright Page 1 of 1

It is certified that error appears in the above-identified patent and that said Letters Patent is hereby corrected as shown below:

In the Claims

In Column 19, Claim 2, Line 35 and 36, delete "Vapor provision means comprising: vapor" and insert -- A Vapor provision means comprising: a vapor --, therefor.

Signed and Sealed this  
Seventeenth Day of September, 2024

Katherine Kelly Vidal  
*Director of the United States Patent and Trademark Office*